US009060993B2

(12) United States Patent
Thompson et al.

(10) Patent No.: US 9,060,993 B2
(45) Date of Patent: Jun. 23, 2015

(54) COMPOSITIONS AND METHODS FOR TREATING CANCER

(75) Inventors: Craig B. Thompson, Merion Station, PA (US); Daniel Bauer, Philadelphia, PA (US); Georgia Hatzivassiliou, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 877 days.

(21) Appl. No.: 10/556,220

(22) PCT Filed: May 7, 2004

(86) PCT No.: PCT/US2004/014263
§ 371 (c)(1),
(2), (4) Date: Dec. 4, 2006

(87) PCT Pub. No.: WO2004/100885
PCT Pub. Date: Nov. 25, 2004

(65) Prior Publication Data
US 2007/0259956 A1    Nov. 8, 2007

Related U.S. Application Data

(60) Provisional application No. 60/469,233, filed on May 9, 2003.

(51) Int. Cl.
*A61K 31/34* (2006.01)
*A61K 51/04* (2006.01)
(52) U.S. Cl.
CPC .............. *A61K 31/34* (2013.01); *A61K 51/0491* (2013.01)

(58) Field of Classification Search
CPC ........................... A61K 31/34; A61K 51/0491
See application file for complete search history.

(56) References Cited

U.S. PATENT DOCUMENTS 5,219,846 A * 6/1993 Bru et al. ...................... 514/118
5,447,954 A * 9/1995 Gribble et al. ................ 514/473
(Continued)

FOREIGN PATENT DOCUMENTS

| WO | WO9322304 | 11/1993 |
| WO | 9402108 | 2/1994 |
| WO | 02070676 | 9/2002 |

OTHER PUBLICATIONS

Ki et al. Radicicol binds and inhibits mammalian ATP Citrate Lyase. The Journal of Biological Chemistry. 2000; 275: 39231-39236.*
(Continued)

*Primary Examiner* — Trevor Love
(74) *Attorney, Agent, or Firm* — Pepper Hamilton LLP

(57) ABSTRACT

Methods of treating individuals identified as having cancer using ATP citrate lyase inhibitor and/or tricarboxylate transporter inhibitor are disclosed. Methods of inducing apoptosis in cancer cells using an ATP citrate lyase inhibitor and/or tri-carboxylate transporter inhibitor are disclosed. of treating an individual who has cancer comprising the steps of identifying the cancer as having a high rate of aerobic glycolysis, and administering an ATP citrate lyase inhibitor and/or tricarboxylate transporter inhibitor are disclosed. Methods of treating individuals who have cancer using compounds that inhibit the expression of ATP citrate lyase or tricarboxylate transporter are disclosed. Methods of identifying a compound with anticancer activity are disclosed.

29 Claims, 20 Drawing Sheets

(56) References Cited

U.S. PATENT DOCUMENTS

| | | | |
|---|---|---|---|
| 5,759,837 A * | 6/1998 | Kuhajda et al. | 435/193 |
| 6,414,002 B1 | 7/2002 | Cheng et al. | |
| 6,727,271 B2 | 4/2004 | Cheng | |
| 6,919,358 B2 | 7/2005 | Cheng | |
| 2002/0094339 A1 * | 7/2002 | Brin et al. | 424/247.1 |

OTHER PUBLICATIONS

Schroder et al, The role of 18F-fluoro-deoxyglucose positron emission tomography (18F-FDG PET) in diagnosis of ovarian cancer, 1999, Int J Gynecol Cancer, 9, pp. 117-122.*

Sonoda, et al, Akt Pathway Activation Converts Anaplastic Astrocytoma to Glioblastoma Multiforme in a Human Astrocyte Model of Glioma, 2001, Cancer Research, 61, 6674-6678 and title page (6 pages in all).*

Wang, et al, Somatic Mutations of PTEN in Glioblastoma Multiforme, 1997, Cancer Research, 57, 4183-4186 and title page (5 pages in all).*

Barth, C., et al "Inhibition of cholesterol synthesis by (-)-hydroxycitrate in perfused rat liver. Evidence for an extramitochondrial mevalonate synthesis from acetyl coenzyme A," *FEBS Lett.* (1972) 22(3):343-346.

Benjamin, W.B., et al. "ATP citrate-lyase and glycogen synthase kinase-3 beta in 3T3-L1 cells during differentiation into adipocytes." *Biochem J.* (1994) 300( Pt 2):477-482.

Berkhout, T.A., et al. "The effect of (-)-hydroxycitrate on the activity of the low-density-lipoprotein receptor and 3-hydroxy-3-methylglutaryl-CoA reductase levels in the human hepatoma cell line Hep G2," *Biochem J.* (1990) 272(1):181-6.

Berwick, D.C., et al. "The identification of ATP-citrate lyase as a protein kinase B (Akt) substrate in primary adipocytes," *J.Biol Chem* (2002) 277(37):33895-900.

Borgelt et al., "The palliation of brain metastases: Final results of the first two studies by the Radiation Therapy Oncology Group." *Int J. Radiat Oncol Biol Phys* (1980) 6(1):1-9.

Czernin, J. "Clinical applications of FDG-PET in oncology." *Acta Medica Austriaca* (2002) 29(5):162-70.

Dolle, R.E., "ATP-citrate lyase as a target for hypolipidemic intervention. Sulfoximine and 3-hydroxy-beta-lactam containing analogues of citric acid as potential tight-binding inhibitors," *J. Med Chem*, (1992) 35(26):4875-4884.

Dolle, R.E., et al. "Synthesis of novel thiol-containing citric acid analogues. Kinetic evaluation of these and other potential active-site-directed and mechanism-based inhibitors of ATP citrate lyase," *J. Med Chem.* (1995) 38(3):537-543.

Elshourbagy, N. A., et al "Rat ATP citrate-lyase. Molecular cloning and sequence analysis of a full-length cDNA and mRNA abundance as a function of diet, organ, and age," *J. Biol Chem* (1990) 265(3):1430-435.

Elshourbagy, N. A., et al. "Cloning and expression of a human ATP-citrate lyase Cdna," *Eur J Biochem.* (1992) 204(2):491-499.

Fang, M. et al., "Citrate and the conversion of carbohydrate into fat. The regulation of fatty acid synthesis by rat liver extracts," *Biochem J.* ( 1967) 105(2):803-11.

Frauwirth, K.A., et al., "The CD28 signaling pathway regulates glucose metabolism," *Immunity* (2002) 16(6):769-777.

Fukuda, H. et al. "Regulation of ATP citrate-lyase gene expression in hepatocytes and adipocytes in normal and genetically obese rats." *J. Biochem* (Tokyo) (1999) 126(2):437-444.

Gribble, A. D., et al. "ATP-citrate lyase as a target for hypolipidemic intervention. Design and synthesis of 2-substituted butanedioic acids as novel, potent inhibitors of the enzyme." *J. Med. Chem.* (1996) 39(18):3569-3584.

Gribble, A.D., et al. "ATP-Citrate lyase as a target for hypolipidemic intervention. 2. Synthesis and evaluation of (3R,5S)-omega-substituted-3-carboxy-3, 5-dihydroxyalkanoic acids and their gamma-lactone prodrugs as inhibitors of the enzyme in vitro and in vivo. " *J. Med Chem.* (1998) 41(19):3582-3595.

Hoffman GE, et al. "Properties and organ distribution of ATP citrate (pro-3S)-lyase." *Biochim Biophys Acta* (1980) 620(1):151-8.

Inoue, H., et al. "Dietary response of the hepatic citrate-cleavage enzyme in hypophysectomized rats "*J Biol Chem.*, 60:93-5, 1966.

Barrow, CJ, et al. "Antimycins, inhibitors of ATP-citrate lyase, from a *Streptomyces* sp,"*Journal of Antibiotics*, (1997) 50(9):729-33.

Kaplan et al, "Purification and characterization of the reconstitutively active tricarboxylate transporter from rat liver mitochondria." *J. Biol Chem.* (1990) 265(22):13379-85.

Law D et al. "Citrate transport in proximal cell line," *Am J. Physiol* (1992) 263(1 Pt 1):C220-5.

Lowenstein, J. M. "Effect of (-)-hydroxycitrate on fatty acid synthesis by rat liver in vivo." *J Biol Chem*, (1971) 246(3):629-32.

Morikawa, J., et al., "Molecular cloning of novel mouse and human putative citrate lyase beta-subunit." *Biochem Biophys Res Commun* (2001) 289(5):1282-6.

Paradies G. et al., "Enhanced activity of the tricarboxylate carrier and modification of lipids in hepatic *mitochondria* from hyperthyroid rats," *Arch Biochem Biophys* (1990) 278(2):425-30.

Pearce, N. J., et al., "The role of ATP citrate-lyase in the metabolic regulation of plasma lipids. Hypolipidaemic effects of SB-204990, a lactone prodrug of the potent ATP citrate-lyase inhibitor SB-201076." *Biochem J* (1998) 334( Pt 1):113-9.

Plas, D. R., et al., "Akt and Bcl-xL promote growth factor-independent survival through distinct effects on mitochondrial physiology," *J Biol. Chem.* (2001) 276(15):12041-8.

Saxty, B. A., et al., "Synthesis and evaluation of (+) and (-)-2,2-difluorocitrate as inhibitors of rat-liver ATP-citrate lyase and porcine-heart aconitase," *Eur J. Biochem.* (1991) 202(3):889-96.

Simpson J.R., et al "Influence of location and extent of surgical resection on survival of patients with glioblastoma multiforme: results of three consecutive Radiation Therapy Oncology Group (RTOG) clinical trials." *Int J. Radiat Oncol Biol Phys* (1993) 26(2):239-44.

Stipani, I et al. "Purification of the active mitochondrial tricarboxylate carrier by hydroxylapatite chromatography." *FEBS Lett* (1983) 161(2):269-74.

Sullivan, A. C., et al "Effect of (-)-hydroxycitrate upon the accumulation of lipid in the rat. II. Appetite." *Lipids* (1974) 9(2):129-34.

Sullivan, A. C., et al. "Effect of (-)-hydroxycitrate upon the accumulation of lipid in the rat. I. Lipogenesis." *Lipids* (1974) 9(2):121-8.

Sullivan AC, et al. "Reactivity and inhibitor potential of hydroxycitrate isomers with citrate synthase, citrate lyase, and ATP citrate lyase." *J Biol Chem* (1977) 252(21):7583-90.

Sullivan, A. C., "(--)-threo-Chlorocitric acid: a novel anorectic agent." *Pharmacol Biochem Behav*, (1981) 15(2):303-10.

Szutowicz A., et al., "Effect of (-)hydroxycitrate on the activities of ATP citrate lyase and the enzymes of acetyl-CoA metabolism in rat brain," *Acta Biochim Pol* (1976) 23(2-3):227-34.

Vander Heiden, M. G., et al., "Bcl-xL regulates the membrane potential and volume homeostasis of mitochondria." *Cell*, (1997) 91(5):627-37.

Vander Heiden, M. G., et al., "Growth factors can influence cell growth and survival through effects on glucose metabolism." *Mol Cell Biol* (2001) 21(17):5899-5912.

Warburg and Negelein, [Uber das Absorptionsspektrum des Atmungsforments], *Biochemische Zeitschrift* (1929), 214, 64-100.

Watson, J. A., et al. "Citrate and the conversion of carbohydrate into fat. Fatty acid synthesis by a combination of cytoplasm and mitochondria." *J. Biol Chem*, (1970) 245(22):5993-6002.

Zara V et al., "Purification and characterization of the tricarboxylate carrier from eel liver mitochondria," *Biochem Biophys Res Commun* (1996) 223(3):508-13.

Perez et al., *Principles and Practice of Radiation Oncology*, 2$^{nd}$ Ed, JB Kippincott Co, Phila (1992).

Database Caplus on STN DN 128:290070, Van Vlijmen et al., *Arzneimittel-Forschung* (1998) 48(4):396-402, Abstract.

Database Caplus on STN, Hildebrandt et al., *Am J Physiol Cell Physiol* (1995) 269/1, 38-1 (C22-C27), Abstract.

(56) References Cited

OTHER PUBLICATIONS

Karzel, K. et al., "The effect of benzenecarboxylic acids—in particular mellitic acid—in in vitro biological system", Arzneimittel-Forschung, 1989, 39:6-11.

Hatzivassiliou, Georgia et al., "ATP citrate lyase inhibition can suppress tumor cell growth", Cancer Cell, 2005, 8:311-321.

Rao et al., "Control of DNA Replication and Cell Growth by Inhibiting the Export of Mitochondrially Derived Citrate", Exp. Cell Res., 1989, 180:341-351.

Salmon, A.S. et al., "PET in Abdominal Pathology: Advantages and Limitations", Abdom Imaging, 2006, 31:174-181.

Son, H. et al., "Role of FDG PET/CT in Staging of Recurrent Ovarian Cancer", RadioGraphics, 2011, 31:569-583.

Chang, J.M. et al., "False Positive and False Negative FDG-PET Scans in Various Thoracic Diseases", Korean J. Radiol, 2006, 7(1):57-69.

Barrington, S.F. and O'Doherty, M.J., "Limitations of PET for Imaging Lymphoma", European Journal of Nuclear Medicine and Molecular Imaging, 2003, 30 (Suppl. 1): S117-S127.

Ho, C.L., "Clinical PET Imaging—An Asian Perspective", Ann Acad Med Singapore, 2004, 33(2): 155-165.

Schoder, H. and Larson, S.M., "Positron Emission Tomography for Prostate, Bladder, and Renal Cancer", Seminars in Nuclear Medicine, 2004, 34(4):274-292.

Gambhir, S.S., "Molecular Imaging of Cancer With Positron Emission Tomography", Nature Reviews, 2002, 2:683-693.

Rose, D.M. et al., "18Fluorodeoxyglucose-Positron Emission Tomograpy in the Management of Patients With Suspected Pancreatic Cancer", Annals of Surgery, 1999, 229 (5):729-738.

Warburg, O., "On the origin of cancer cells", Science, 1956, 123(3191):309-314.

* cited by examiner

Structure of a potent ACL inhibitor and its prodrug

SB-201076

SB-204990

Figure 1  Structure of SB-201076 and its γ-lactone SB-204990

Pierce N.J., et al. (1998) The role of ATP citrate-lyase in the metabolic regulation of plasma lipids. Biochem J. 334, p113-119

US 9,060,993 B2

COMPOSITIONS AND METHODS FOR TREATING CANCER

CROSS-REFERENCE TO RELATED APPLICATIONS

This application is a national stage application of PCT International Application PCT/US2004/014263, filed May 7, 2004, which claims priority to U.S. Provisional Patent Application 60/469,233, filed May 9, 2003.

FIELD OF THE INVENTION

The present invention relates to compositions comprising inhibitors of ATP citrate lyase and/or tricarboxylate transporter and methods of using such compositions to treat individuals who have been diagnosed with cancer.

BACKGROUND OF THE INVENTION

Each year, more than one million invasive cancers are diagnosed in the United States alone. Despite improvements in treatments and many successes, cancer continues to be a significant cause of death and incalculable suffering.

Considerable evidence suggests that cancer cells have metabolic requirements that are distinctly different from those of the vast majority of somatic cells. Although the differences in the metabolic requirements of cancer cells have been exploited to therapeutic advantage in certain specific malignancies such as L-asparaginase in childhood leukemia, no generalized mechanism to exploit the unique metabolism of cancer cells has been devised.

There remains a need for additional drugs and methods for treating cancer.

SUMMARY OF THE INVENTION

The present invention relates to methods of treating an individual who has cancer comprising the steps of identifying the cancer as a cancer that comprises cancer cells that have a high rate of aerobic glycolysis, and subsequently administering to the individual a therapeutically effective amount of an ATP citrate lyase inhibitor.

The present invention further relates to methods of treating individuals identified as having cancer. The methods comprise the step of administering to individuals a therapeutically effective amount of an ATP citrate lyase inhibitor that is effective to induce apoptosis in greater than 50% of cells in an in vitro apoptosis assay at a concentration of less than 1 mM.

The present invention further relates to methods of inducing apoptosis in cancer cells comprising the step of delivering to cancer cells an amount of an ATP citrate lyase inhibitor effective to induce apoptosis in said cell. The ATP citrate lyase inhibitor is effective to induce apoptosis in greater than 50% of cells in an in vitro apoptosis assay at a concentration of less than 1 mM.

The present invention further relates to methods of treating individuals identified as having cancer in which cancer comprises cells that are not dependent on endogenously synthesized fatty acid. The methods comprise the step of administering to the individual a therapeutically effective amount of an ATP citrate lyase inhibitor.

The present invention further relates to methods of inducing apoptosis in cancer cells that are not dependent on endogenously synthesized fatty acid. The methods comprise the step of delivering to the cancer cell an amount of an ATP citrate lyase inhibitor effective to induce apoptosis in the cell.

The present invention further relates to methods of treating individuals identified as having cancer. The methods comprise the step of administering to the individual a therapeutically effective amount of a tricarboxylate transporter inhibitor.

The present invention further relates to methods of inducing apoptosis in cancer cells comprising the step of delivering to cancer cells an amount of a tricarboxylate transporter inhibitor effective to induce apoptosis in cells.

The present invention further relates to methods of treating individuals who have cancer comprising the steps of identifying the cancer as a cancer that comprises cancer cells that have a high rate of aerobic glycolysis, and subsequently administering to the individual a therapeutically effective amount of a tricarboxylate transporter inhibitor.

The present invention further relates to methods of treating individuals who have been identified as having cancer comprising administering to the individual a therapeutically effective amount of a compound which inhibits the expression of ATP citrate lyase or tricarboxylate transporter.

The present invention further relates to methods identifying compounds with anticancer activity. The methods comprise the steps of: identifying a test compound as an inhibitor of ATP citrate lyase or tricarboxylate transporter and performing an apoptosis assay to determine if said test compound induces apoptosis.

DESCRIPTION OF PREFERRED EMBODIMENTS

Definitions

Figure 1:
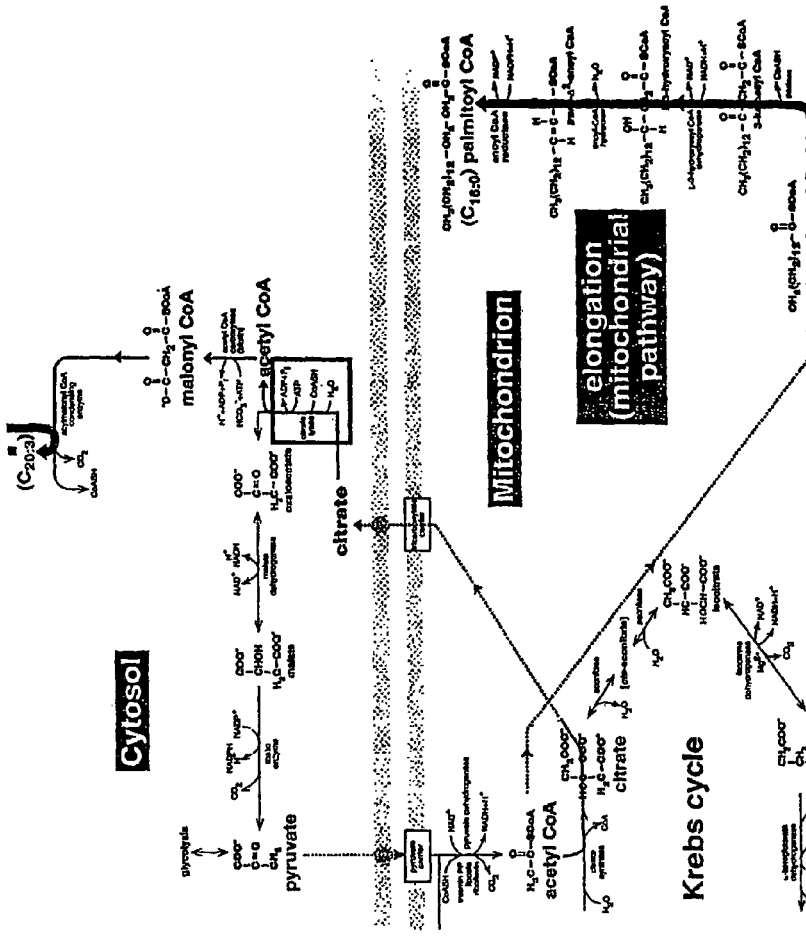
FIG. 1 depicts metabolic pathways.

As used herein, the terms "an individual identified as having cancer" and "cancer patient" are used interchangeably and are meant to refer to an individual who has been diagnosed as having cancer. There are numerous well known means for identifying an individual who has cancer. In some embodiments, a cancer diagnosis is made or confirmed using PET imaging. Some embodiments of the invention comprise the step of identifying individuals who have cancer.

As used herein, the term "cancer characterized by a high rate of aerobic glycolysis" refers to cancer having cells which exhibit a higher rate of aerobic glycolysis than those of the tissues surrounding it do. Such cancer cells take up above-average quantities of glucose from the environment. Cancer characterized by a high rate of aerobic glycolysis can be identified using PET imaging technology, preferably with $^{18}$fluoro-deoxyglucose. The positive detection of a tumor using such a test indicates that the cancer is characterized by a high rate of aerobic glycolysis. PET methodologies are set forth in Czernin, J. 2002 Acta Medica Austriaca 29:162-170, which is incorporated herein by reference.

As used herein, the term "ATP citrate lyase inhibitor" is meant to refer to a compound that is capable of inhibiting ATP citrate lyase activity. The compound can be a small molecule, large molecule, peptide, oligonucleotide, and the like.

As used herein, the term "tricarboxylate transporter inhibitor" is meant to refer to a compound that is capable of inhibiting tricarboxylate transporter activity. The compound can be a small molecule, large molecule, peptide, oligonucleotide, and the like.

As used herein, the term "therapeutically effective amount" is meant to refer to an amount of an active agent or combination of agents effective to ameliorate or prevent the symptoms, shrink tumor size, or prolong the survival of the patient being treated. Determination of a therapeutically effective amount is well within the capabilities of those skilled in the art, especially in light of the detailed disclosure provided herein.

As used herein, the term "in vitro apoptosis assay" is meant to refer to the assay to assess and measure the ability of a compound to induce apoptosis in cultured cells Metabolism in Cancer Cells with a High Rate of Aerobic Glycolysis and the Induction of Apoptosis in Such Cells The present invention arises from the observation that many human cancers display a high rate of aerobic glycolysis and that this high rate of aerobic glycolysis leads to increasing dependence of the cancer cells on certain metabolic enzymes that are not normally required for the survival of vegetative cells. An exploration was undertaken to determine whether or not the increasing dependence on such enzymes leads cancer cells to be susceptible to treatment with inhibitors of such enzymes. One key feature of cancer cells that display a high rate of aerobic glycolysis because of excessive uptake of glucose from their environment is that the cells produce a huge quantity of pyruvate. The import of such pyruvate into the mitochondrial matrix and its further degradation by the pyruvate dehydrogenase complex results in increased acetyl-CoA entering into the tricarboxylic acid cycle (TCA). If the NADH produced from the TCA cycle exceeds that needed to maintain electron transport and cellular ATP production through oxidative phosphorylation, progressive mitochondrial hyperpolarization and increased reactive oxygen species (ROS) production from the electron transport chain can result. Mitochondrial hyperpolarization and increased ROS production from the electron transport chain ultimately results in apoptosis of the cell (Vander Heiden, M. G., et al. Cell, 91:627-637, 1997, which is incorporated herein by reference).

Although increased NADH can act as an allosteric inhibitor of several enzymes in the TCA cycle, cancer cells appear to deal with the increased load of acetyl-CoA produced by metabolism of pyruvate primarily by exporting the end product of the first reaction in the TCA cycle, citrate, into the cytosol. Citrate is formed by the condensation of acetyl-CoA and oxaloacetate. The resulting citrate can be exported from the mitochondria down a concentration gradient through the transport activity of the tricarboxylate transporter. In the cytosol, citrate can be reconverted to oxaloacetate and acetyl-CoA as a result of the activities of ATP citrate lyase (ACL). The further metabolism of oxaloacetate in the cytosol produces NADPH for cellular synthetic reactions and pyruvate, which can be reimported into the mitochondria for regeneration of oxaloacetate. The cytosolic acetyl-CoA can be utilized by a growing cell to produce key growth substrates and for: 1) the N-acetylation of proteins to increase protein stability, 2) the maintenance of active chromatin through acetylation of histones and transcriptional regulatory factors, 3) the lipid modification of membrane proteins via prenylation and acylation and 4) the synthesis of bulk lipids including sterols, sphingolipids and phospholipids. Pentanyl pyrophosphate is required for lipid modifications of proteins through palmitylation, geranylgeranylation, or farnesylation, as well as for the intracellular production of sphingomyelin.

It has been suggested that the role of ATP citrate lyase is restricted to the production of cytosolic acetyl-CoA and NADPH in liver and adipose tissue which are used in these tissues for the production of long chain fatty acids (FIG. 1) (Elshourbagy, N. A., et al, J Biol Chem, 265: 1430-1435, 1990; Elshourbagy, N. A., et al. Eur J Biochem, 204: 491-499, 1992, and Fukuda, H. et al. J Biochem (Tokyo), 126: 437-444, 1999, which are each incorporated herein by reference). Consistent with this view, previous work has suggested that ATP citrate lyase is primarily expressed in lipogenic tissues. Other vegetative tissues express little to no levels of the enzyme.

In characterizing tumor cell lines, it has been discovered that a feature of growing cells is the induction of a high level of ATP citrate lyase activity. Data indicates a role for ATP citrate lyase in preventing mitochondrial hyperpolarization and ROS production from the electron transport chain. In addition, an investigation was undertaken to determine whether the induction of ATP citrate lyase is required for cell growth because ATP citrate lyase appears to be the major enzyme involved in the synthesis of cytosolic acetyl-CoA in tissues other than liver. In simple organisms the primary generation of cytosolic acetyl-CoA occurs through acetyl-CoA synthetase using acetate as a precursor. However, because of the metabolic activities of liver relatively little acetate is available to growing cells in mammalian tissues. As a result of the required increase in protein synthesis, the need to maintain an active chromatin structure through histone acetylation, and the need to produce specialized lipids for activation of signal transduction proteins through palmitylation, geranylgeranylation, or farneslyation, as well as the assembly of signaling complexes through the production of sphingomyelin:cholesterol rafts within lipid membranes, growing cells require a high level of cytosolic acetyl-CoA. Data indicates that this high level production of acetyl-CoA required for cellular growth requires growth factor or oncogene-stimulated glycolysis, increased mitochondrial production of citrate, and the activity of ATP citrate lyase. These data indicate that inhibition of ATP citrate lyase prevents the growth and leads to mitochondrially-induced apoptosis of transformed cells.

Data provide evidence of the efficacy of inhibiting ATP citrate lyase in inhibiting cancer cell growth and in inducing cell death of transformed cells. Furthermore, this method has the benefit of selectivity in that non-growing somatic cells are relatively resistant to the effect of ATP citrate lyase inhibitors and non-transformed cells can adapt to ATP citrate lyase inhibition through cell cycle arrest.

Inhibition of the tricarboxylate transporter is an alternative way to inhibit cancer cell growth and to induce cell death of transformed cells. Such inhibition reduces or prevents citrate export to the cytosol, and ultimately leads to the conditions and events described above which result in apoptosis of the cell.

Treatment of Cancer Patients with ATP Citrate Lyase Inhibitors

Several embodiments of the invention include the use of ATP citrate lyase inhibitor to treat cancer.

Embodiments of the present invention are particularly useful to treat individuals who have cancer identified as having a high rate of aerobic glycolysis. In some embodiments, methods for treating an individual who has cancer comprise the steps of first identifying cancer as having a high rate of aerobic glycolysis and then administering to such an individual a therapeutically effective amount of an ATP citrate lyase inhibitor. In some preferred embodiments, the identification of cancer as having a high rate of aerobic glycolysis is done by PET imaging, preferably using $^{18}$fluoro-deoxyglucose. In some embodiments, the ATP citrate lyase inhibitor is effective to induce apoptosis in greater than 50% of cells in an in vitro apoptosis assay at a concentration of less than 1 mM. In some embodiments, the ATP citrate lyase inhibitor is effective to induce apoptosis in greater than 50% of cells in an in vitro apoptosis assay at a concentration of less than 0.1 mM. In preferred embodiments, the ATP citrate lyase inhibitor is effective to induce apoptosis in greater than 50% of cells in an in vitro apoptosis assay at a concentration of less than 50 µM.

In some embodiments of the present invention, methods for treating an individual who has been identified as having cancer comprise administering to such an individual a therapeutically effective amount of an ATP citrate lyase inhibitor which is known to be effective to induce apoptosis in greater than 50% of cells in an in vitro apoptosis assay at a concentration of less than 1 mM. In some preferred embodiments, the ATP citrate lyase inhibitor is effective to induce apoptosis in greater than 50% of cells in an in vitro apoptosis assay at a concentration of less than 0.1 mM. In some preferred embodiments, the ATP citrate lyase inhibitor is effective to induce apoptosis in greater than 50% of cells in an in vitro apoptosis assay at a concentration of less than 50 µM. In some preferred embodiments, prior to administration of ATP citrate lyase inhibitor, the cancer is confirmed as being a cancer characterized by a high rate of aerobic glycolysis. The preferred method of doing so is be PET imaging, preferably using $^{18}$fluoro-deoxyglucose.

Methods are provided for inducing apoptosis in a cancer cell. The methods comprise delivering to the cancer cell an amount of an ATP citrate lyase inhibitor effective to induce apoptosis in the cell. The ATP citrate lyase inhibitor used is effective to induce apoptosis in greater than 50% of cells in an in vitro apoptosis assay at a concentration of less than 1 mM. In some embodiments, the ATP citrate lyase inhibitor is effective to induce apoptosis in greater than 50% of cells in an in vitro apoptosis assay at a concentration of less than 0.1 mM. In some preferred embodiments, the ATP citrate lyase inhibitor is effective to induce apoptosis in greater than 50% of cells in an in vitro apoptosis assay at a concentration of less than 50 µM.

Embodiments of the present invention are particularly useful to treat patients who have cancer with cancer cells that are not dependent on endogenously synthesized fatty acid. Such cancers include most cancers and generally exclude those cancers arising from tissues associated with lipid production such as liver cancer, and cancer involving fat cells. Cancer cells that are dependent on endogenously synthesized fatty acid are generally limited to hepatomas, lipomas and liposarcomas. Thus, some methods of the invention relate to methods of treating a cancer patient who has cancer that is not dependent on endogenously synthesized fatty acid (i.e cancer cells which can use exogenously synthesized fatty acid) wherein such methods comprise the step of administering to such an individual a therapeutically effective amount of an ATP citrate lyase inhibitor. In preferred embodiments, the ATP citrate lyase inhibitor is known to be effective to induce apoptosis in greater than 50% of cells in an in vitro apoptosis assay at a concentration of less than 0.1 mM. In some preferred embodiments, the ATP citrate lyase inhibitor is effective to induce apoptosis in greater than 50% of cells in an in vitro apoptosis assay at a concentration of less than 0.1 mM. In some preferred embodiments, the ATP citrate lyase inhibitor is effective to induce apoptosis in greater than 50% of cells in an in vitro apoptosis assay at a concentration of less than 50 µM. Cancer cells that are dependent on endogenously synthesized fatty acid generally have high levels of fatty acid synthase. Endogenous fatty acid synthesis in such cells typically occurs at a rate of incorporation of greater than 10 fmoles of acetyl-CoA into acyl glyceride per 200,000 cells per minute. In some preferred embodiments, prior to administration of ATP citrate lyase inhibitor, the cancer is confirmed as being a cancer characterized by a high rate of aerobic glycolysis. The preferred method of doing so is be PET imaging, preferably using $^{18}$fluoro-deoxyglucose.

Methods are provided for inducing apoptosis in a cancer cell that is not dependent on endogenously synthesized fatty acid. The methods comprise delivering to the cancer cell an amount of an ATP citrate lyase inhibitor effective to induce apoptosis in the cell. The ATP citrate lyase inhibitor used is effective to induce apoptosis in greater than 50% of cells in an in vitro apoptosis assay at a concentration of less than 1 mM. In some preferred embodiments, the ATP citrate lyase inhibitor is effective to induce apoptosis in greater than 50% of cells in an in vitro apoptosis assay at a concentration of less than 0.1 mM. In some preferred embodiments, the ATP citrate lyase inhibitor is effective to induce apoptosis in greater than 50% of cells in an in vitro apoptosis assay at a concentration of less than 50 µM.

ATP Citrate Lyase Inhibitors

Figure 4:
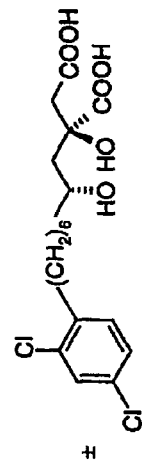
FIG. 4 discloses structures of ATP citrate lyase inhibitors useful in some embodiments of the invention.
Figure 4:
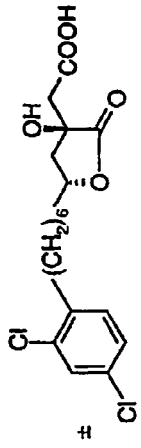
Figure 5:
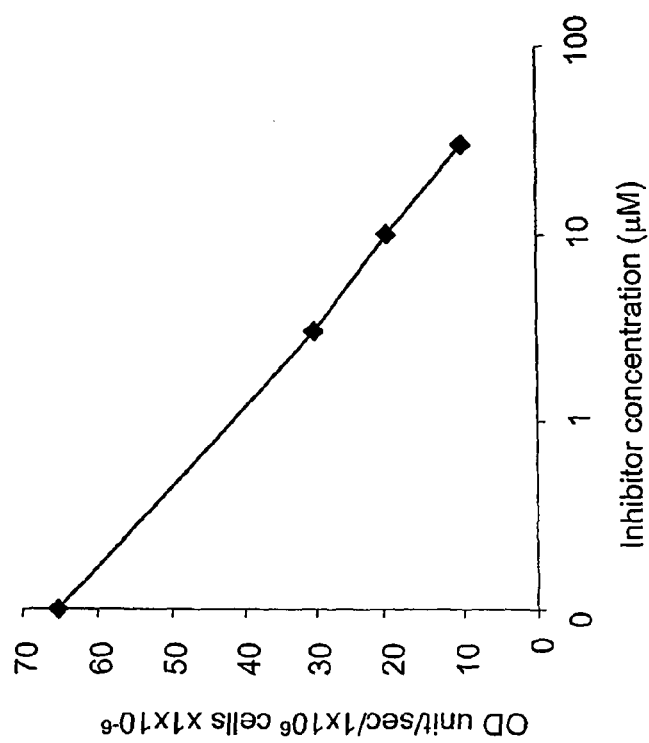

There are many examples of ATP citrate lyase inhibitors in the art. Each of U.S. Pat. No. 5,447,954 issued Sep. 5, 1995 to Gribble et al., U.S. Pat. No. 6,414,002 issued Jul. 2, 2002 to Cheng et al., U.S. Application Publication Number 20030087935A1 by Cheng et al. published May 8, 2003, U.S. Application Publication Number 20030069275 A1 by Cheng et al. published Apr. 10, 2003, and Barrow, et al., "Antimycins, Inhibitors of ATP-Citrate Lyase, from a *Streptomyces* sp.", Journal of Antibiotics, vol. 50, No. 9, pp. 729 (1997), which are each incorporated herein by reference, disclose compounds that are ATP citrate lyase inhibitors. In a preferred embodiment, the ATP citrate lyase inhibitor is selected from the group consisting of compounds having a structure defined by the formula: set forth in U.S. Pat. No. 5,447,954 as structure I, preferably a compound having one of the specifically described structures disclosed therein, preferably a compound specifically in an Example set forth therein, preferably a compound having a structure set forth in FIG. 4 herein. Other known inhibitors include (−)hydroxycitrate, (R,S)-S-(3,4-dicarboxy-3-hydroxy-3-methyl-butyl)-CoA, and S-carboxymethyl-CoA.

The determination of whether or not a compound is an ATP citrate lyase inhibitor is within the skill of one of ordinary skill in the art. Examples of assays useful to identify ATP citrate lyase inhibitors include those described in Hoffmann G E, et al. Biochim Biophys Acta 1980 Oct. 6; 620(1):151-8; Szutowicz A, et al. Acta Biochim Pol 1976; 23(2-3):227-34; and Sullivan A C, et al. J Biol Chem 1977 Nov. 10; 252(21): 7583-90, which are each incorporated herein by reference. An example of how one would determine if a compound is an ATP citrate lyase inhibitor would be to isolate the ATP citrate lyase protein. The protein can be isolated from cells where the ATP citrate lyase is naturally expressed or where it has been overexpressed by means of transfection of a genetic construct or infection with a virus that directs the expression of the ATP citrate lyase protein. The nucleic acid sequence of the MRNA that encodes ATP citrate lyase is Genbank Accession number U18197, which is incorporated herein by reference. Additionally ATP citrate lyase can also be expressed recombinantly. Upon isolating the protein a person of ordinary skill in the art can measure its activity in the presence or absence of a potential ATP citrate lyase inhibitor, preferably using positive and/or negative controls. If the activity is less in the presence than in the absence of an alleged inhibitor, that compound is an ATP citrate lyase inhibitor. To confirm a compound is a ATP citrate lyase inhibitor useful to treat cancer, the compound may be further tested in a routine apoptosis assay to confirm and assess its activity to induce apoptosis.

Treatment of Cancer Patients with Tricarboxylate Transporter Inhibitors

Several embodiments of the invention include the use of tricarboxylate transport inhibitors to treat cancer.

In some embodiments of the present invention, methods for treating an individual who has been identified as having cancer comprise administering to such an individual a therapeutically effective amount of a tricarboxylate transport inhibitor. In some embodiments, the methods of the present invention are particularly useful to treat patients who have cancer with cancer cells that are not dependent on endogenously synthesized fatty acid. In some preferred embodiments, prior to administration of tricarboxylate transport inhibitor, the cancer is confirmed as being a cancer characterized by a high rate of aerobic glycolysis. The preferred method of doing so is PET imaging, preferably using $^{18}$fluoro-deoxyglucose.

Methods for treating an individual who has cancer may comprise the steps of identifying cancer as having a high rate of aerobic glycolysis and then administering to such an individual a therapeutically effective amount of a tricarboxylate transport inhibitor. The preferred method of identifying cancer as having a high rate of aerobic glycolysis is by PET imaging, preferably using $^{18}$fluoro-deoxyglucose.

Methods are provided for inducing apoptosis in a cancer cell. The methods comprise delivering to the cancer cell an amount of a tricarboxylate transport inhibitor effective to induce apoptosis in the cell.

Tricarboxylate Transporter Inhibitors

There are many examples of tricarboxylate transporter inhibitors in the art. Such examples include: 1,2,3-benzenetricarboxylate, isocitrate, malate, phosphoenolpyruvate, n-butylmalonate, sulfhydryl reagents, diethyl pyrocarbonate, 2,3-butanedione, phenylglyoxal, pyridoxal, 5-phosphate dicarboxylates, succinate, malate, oxaloacetate, tricarboxylates isocitrate, tricarballylate and palmitoyl-CoA.

The determination of whether or not a compound is a tricarboxylate transporter inhibitor is within the skill of one of ordinary skill in the art. An example of how one would determine if a compound is a tricarboxylate transporter inhibitor would be to isolate the tricarboxylate transporter protein, methods of which are disclosed in Kaplan et al, J Biol Chem 1990 Aug. 5; 265(22):13379-85; Zara V et al. Biochem Biophys Res Commun 1996 Jun. 25; 223(3):508-13; Stipani, I et al. FEBS Lett 1983 Sep. 19; 161(2):269-74, which are each incorporated herein by reference. The protein can be isolated from cells where the tricarboxylate transporter is naturally expressed or where it has been overexpressed by means of transfection of genetic construct or infection with a virus that directs the expression of the tricarboxylate transporter protein. Additionally tricarboxylate transporter can also be expressed recombinantly in a host cell. Upon isolating the protein a person of ordinary skill in the art can measure its activity in the presence or absence of a potential tricarboxylate transporter inhibitor, preferably using positive and/or negative controls. If the tricarboxylate transporter activity is less in the presence than in the absence of an alleged inhibitor, that compound is a tricarboxylate transporter inhibitor Alternatively, assays can be performed using cells or mitochondria as described in Law D et al. Am J Physiol 1992 Jul.; 263(1 Pt 1):C220-5; and Paradies G et al. Arch Biochem Biophys 1990 May 1; 278(2):425-30, which are each incorporated herein by reference. To confirm a compound is a tricarboxylate transporter inhibitor useful to treat cancer, the compound may be further tested in a routine apoptosis assay to confirm and assess its activity to induce apoptosis.

Apoptosis Assays

Apoptosis can be detected by many procedures that are well known to those of ordinary skill in the art. Examples of methods to detect apoptosis include, without limitation, TUNEL Assay, measuring caspase activity, Annexin-V staining, and the like. Apoptosis activity is measured as set forth in the assay described in Example 1.

Combination Therapies

In some embodiments, an ATP citrate lyase inhibitor and/or tricarboxylate transporter inhibitor can be co-administered with other therapeutics and/or part of a treatment regimen that includes radiation therapy.

The co-administration of therapeutics can be sequential in either order or simultaneous. In some embodiments an ATP citrate lyase inhibitor and/or tricarboxylate transport inhibitor is co-administered with more than one additional therapeutic. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platin, vindesine (and other vinca alkaloids), mitomycin and bleomycin. Other chemotherapeutics include: purothionin (barley flour oligopeptide), macromomycin. 1,4-benzoquinone derivatives and trenimon. Anti-cancer antibodies, such as herceptin, and toxins are also examples of other additional therapeutics.

The therapeutic regimens can include sequential administration of an ATP citrate lyase inhibitor and/or tricarboxylate transport inhibitor and initiation of radiation therapy in either order or simultaneously. Those skilled in the art can readily formulate an appropriate radiotherapeutic regimen. Carlos A Perez & Luther W Brady: Principles and Practice of Radiation Oncology, 2nd Ed. JB Lippincott Co, Phila., 1992, which is incorporated herein by reference describes radiation therapy protocols and parameters which can be used in the present invention. For GBMs (glioblastoma, the most malignant glial brain tumor), Simpson W. J. et al.: Influence of location and extent of surgical resection on survival of patients with glioblastoma multiforms: Results of three consecutive Radiation Therapy Oncology Group (RTOG) clinical trials. Int J Radiat Oncol Biol Phys 26:239-244, 1993, which is incorporated herein by reference describes clinical protocols useful in the methods of the present invention. Similarly, for Borgelt et al., The palliation of brain metastases: Final results of the first two studies of the Radiation Therapy Oncology Group. Int J Radiat Oncol Biol Phys 6:1-9, 1980, which is incorporated herein by reference, describes clinical protocols useful in the methods of the present invention. In some preferred embodiments, radiation therapy using gamma radiation is provided.

When used in as part of the combination therapy the therapeutically effective amount of the inhibitor may be adjusted such that the amount is less than the dosage required to be effective if used without other therapeutic procedures.

In some preferred embodiments, treatment with pharmaceutical compositions according to the invention is preceded by surgical intervention.

Pharmaceutical Compositions and Routes of Administration

The pharmaceutical composition may be formulated by one having ordinary skill in the art with compositions selected depending upon the chosen mode of administration. Suitable pharmaceutical carriers are described in the most recent edition of Remington's Pharmaceutical Sciences, A. Osol, a standard reference text in this field.

Administering the pharmaceutical composition can be effected or performed using any of the various methods known to those skilled in the art. Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Injectables are sterile and pyrogen free. Alternatively, the compounds may be in powder form for constitution with a suitable vehicle, e.g., sterile pyrogen-free water, before use. For transmucosal administration, penetrants appropriate to the barrier to be permeated are used in the formulation. Such penetrants are generally known in the art.

For parenteral administration, the ATP citrate lyase inhibitor or tricarboxylate transport inhibitor can be, for example, formulated as a solution, suspension, emulsion or lyophilized powder in association with a pharmaceutically acceptable parenteral vehicle. Examples of such vehicles are water, saline, Ringer's solution, dextrose solution, 5% human serum albumin, Ringer's dextrose, dextrose and sodium chloride, lactated Ringer's and fixed oils, polyethylene glycol, polyvinyl pyrrolidone, lecithin, arachis oil or sesame oil. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. Parenteral dosage forms may be prepared using water or another sterile carrier. For example, a parenteral composition suitable for administration by injection is prepared by dissolving 1.5% by weight of active ingredient in 0.9% sodium chloride solution. Alternatively, the solution can be lyophilised and then reconstituted with a suitable solvent just prior to administration.

Pharmaceutically acceptable carriers are well known to those skilled in the art and include, but are not limited to, 0.01-0.1 M and preferably 0.05 M phosphate buffer or 0.8% saline. Intravenous carriers include fluid and nutrient replenishers, electrolyte replenishers such as those based on Ringer's dextrose, and the like. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media.

The pharmaceutical compositions can be prepared using conventional pharmaceutical excipients and compounding techniques. Oral dosage forms may be elixers, syrups, tablets, pills, dragees, capsules, liquids, gels, syrups, slurries, suspensions and the like, for oral ingestion by a patient to be treated. The typical solid carrier may be an inert substance such as lactose, starch, glucose, cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; binding agents, magnesium sterate, dicalcium phosphate, mannitol and the like. A composition in the form of a capsule can be prepared using routine encapsulation procedures. For example, pellets containing the active ingredient can be prepared using standard carrier and then filled into a hard gelatin capsule; alternatively, a dispersion or suspension can be prepared using any suitable pharmaceutical carrier(s), for example, aqueous gums, celluloses, silicates or oils and the dispersion or suspension then filled into a soft gelatin capsule. Typical liquid oral excipients include ethanol, glycerol, glycerine, non-aqueous solvent, for example, polyethylene glycol, oils, or water with a suspending agent, preservative, flavoring or coloring agent and the like. All excipients may be mixed as needed with disintegrants, diluents, lubricants, and the like using conventional techniques known to those skilled in the art of preparing dosage forms. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, and the like formulated in conventional manner. The compounds may also be formulated in rectal or vaginal compositions such as suppositories or enemas. A typical suppository formulation comprises a binding and/or lubricating agent such as polymeric glycols, glycerides, gelatins or cocoa butter or other low melting vegetable or synthetic waxes or fats. For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The formulations may also be a depot preparation which can be administered by implantation (for example subcutaneously or intramuscularly) or by intramuscular injection. In such embodiments, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The compounds used in the invention may also be formulated for parenteral administration by bolus injection or continuous infusion and may be presented in unit dose form, for instance as ampoules, vials, small volume infusions or prefilled syringes, or in multi-dose containers with an added preservative.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

Dosages and Treatment Regimens

According to the present invention, methods of treating cancer in individuals who have been identified as having cancer are performed by delivering to such individuals an amount of an ATP citrate lyase inhibitor or tricarboxylate transporter inhibitor sufficient to induce apoptosis in tumor cells in the individual. By doing so, the tumor cells will undergo apoptosis and the tumor itself will reduce in size or be eliminated entirely. Thus, Patient survival may be extended and/or quality of life improved as compared to treatment that does not include ATP citrate lyase inhibitor or tricarboxylate transporter inhibitor administration in apoptosis inducing doses. The present invention provides for methods of inducing apoptosis in cancer cells comprising the step of delivering an citrate lyase inhibitor or tricarboxylate transporter inhibitor to such cells in an amount effective to induce apoptosis.

The pharmaceutical compositions described above may be administered by any means that enables the active agent to reach the agent's site of action in the body of the individual. The dosage administered varies depending upon factors such as: pharmacodynamic characteristics; its mode and route of administration; age, health, and weight of the recipient; nature and extent of symptoms; kind of concurrent treatment; and frequency of treatment.

The amount of compound administered will be dependent on the subject being treated, on the subject's weight, the severity of the affliction, the manner of administration and the judgment of the prescribing physician. In some embodiments, the dosage range would be from about 1 to 3000 mg, in particular about 10 to 1000 mg or about 25 to 500 mg, of active ingredient, in some embodiments 1 to 4 times per day, for an average (70 kg) human. Generally, activity of individual compounds used in the invention will vary.

Dosage amount and interval may be adjusted individually to provide plasma levels of the compounds which are sufficient to maintain therapeutic effect. Usually, a dosage of the active ingredient can be about 1 microgram to 100 milligrams per kilogram of body weight. In some embodiments a dosage is 0.05 mg to about 200 mg per kilogram of body weight. In another embodiment, the effective dose is a dose sufficient to deliver from about 0.5 mg to about 50 mg. Ordinarily 0.01 to 50 milligrams, and in some embodiments 0.1 to 20 milligrams per kilogram per day given in divided doses 1 to 6 times a day or in sustained release form is effective to obtain desired results. In some embodiments, patient dosages for administration by injection range from about 0.1 to 5 mg/kg/day, preferably from about 0.5 to 1 mg/kg/day. Therapeutically effective serum levels may be achieved by administering multiple doses each day. Treatment for extended periods of time will be recognized to be necessary for effective treatment.

In some embodiments, the route may be by oral administration or by intravenous infusion. Oral doses generally range from about 0.05 to 100 mg/kg, daily. Some compounds used in the invention may be orally dosed in the range of about 0.05 to about 50 mg/kg daily, while others may be dosed at 0.05 to about 20 mg/kg daily. Infusion doses can range from about 1.0 to $1.0 \times 10^4$ microgram/kg/min of inhibitor, admixed with a pharmaceutical carrier over a period ranging from several minutes to several days.

Inhibition of Expression

The present invention additionally relates to methods of treating cancer by inhibiting expression of ATP citrate lyase or tricarboxylate transporter. Inhibition of expression can be accomplished using antisense, RNAi technology or ribozymes to prevent production of ATP citrate lyase or tricarboxylate transporter in the cancer cell. Those skilled in the art can make and use such compounds in therapeutically effective amounts in place of the inhibitors described herein in order to practice the various embodiments of the invention as disclosed herein.

Species

In addition to humans, the methods of the present invention may be employed to treat other species of animal suffering from cancer including, for example, canine, feline, equine, porcine, bovine and ovine species.

EXAMPLES

Example 1

In vitro Apoptosis Assay

Remove 500 µl of treated or untreated cells (at concentrations of $0.5-1\times10^6$ cells/ml) to a FACS tube and add 50 µl of 10× Annexin V binding buffer (BD Biosciences Pharmingen, San Diego, Calif.) to each tube. Stain cells with Annexin V-FITC (BD Biosciences Phanningen, San Diego, Calif.) using 4 µl Annexin V-FITC and propidium iodide (Molecular Probes, Eugene, Oreg.) at a final concentration of 3 µg/ml of cells. The cells are preferably hematopoietic IL3-dependent cell lines such as for example IL3-dependent FL5.12 pro-B cells transfected with different transgenes (Bcl-xL, myrAkt) or vector control plasmids and IL3-dependent cells isolated from the bone marrow of Bax−/−Bak−/− knockout mice. Incubate at 37° for 30 minutes. Perform flow cytometry. Early apoptotic cells are Annexin V positive, propidium iodide negative while late apoptotic cells are both Annexin V and propidium iodide positive.

Example 2

ATP Citrate Activity is Upregulated in Proliferating Cells by both Transcriptional/Translational and Post-Translational Mechanisms.

Figure 2:
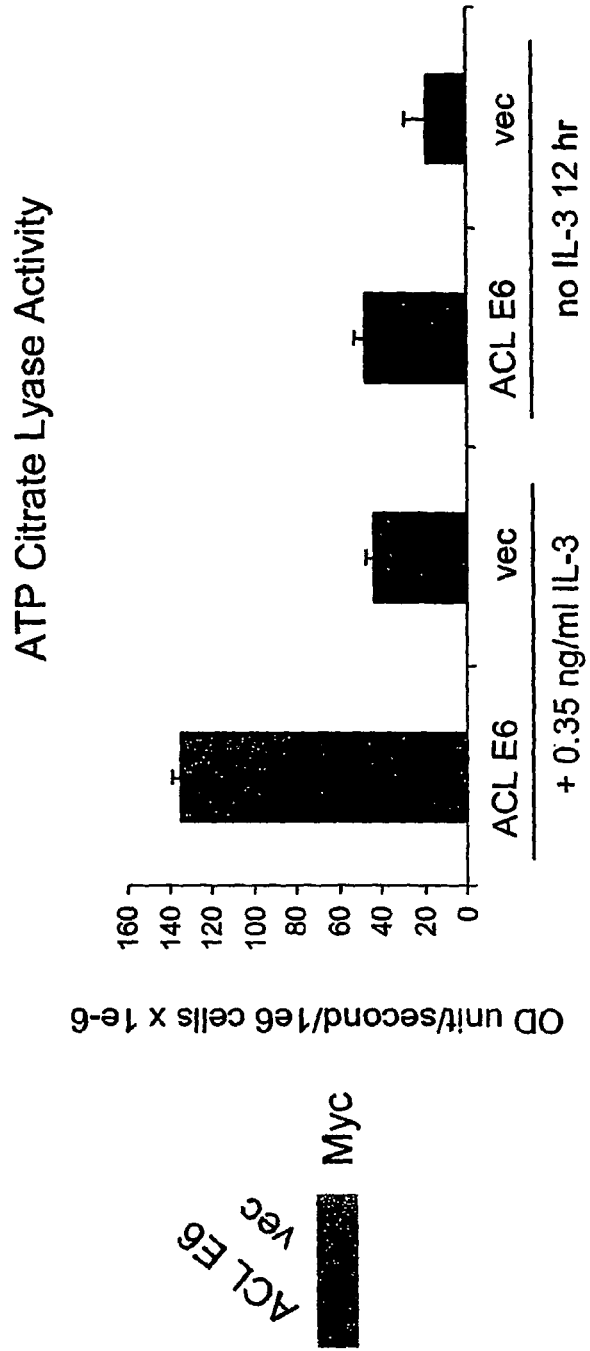
FIGS. 2, 3, 5-11, 12A, 12B, 13, 14A, 14B and 15-18 depict data generated in experiments described in Example 2.

To investigate the potential induction of ATP citrate lyase in response to mitogen stimulation of cell proliferation, an assay was developed to quantitate ATP citrate lyase (ACL) activity in cellular extracts. As a positive control, stable transfectants of a cell line dependent on IL-3 for the induction of cell proliferation was also produced. The cytosolic extracts from the wild type cells and ATP citrate lyase transfected cells were analyzed by determining the level of ATP citrate lyase activity per $10^6$ cells as determined by the malate dehydrogenase catalyzed reduction of oxaloacetate by NADH. NADH consumption was measured by monitoring the reaction at 340 nm. Assays were run by providing citrate at 100 µM in the presence of 5 mM ATP and 300 µM of CoA. As a positive control, ACL-transfected cells displayed a 3.5-fold increase in ATP citrate lyase activity demonstrating validity of the assay (FIG. 2). When the growth factor IL-3 was removed from the cultures, inducing a cell cycle arrest from the cells at 12 hours following withdrawal, a pronounced decline in ACL activity was observed in both vector controlled and ACL-transfected cells. Together, these suggest that ACL activity is induced in proliferating cells and that the ACL activity in cells transfected with ACL can be modified post-translationally as a result of events associated with mitogen-activated cells.

Figure 3:
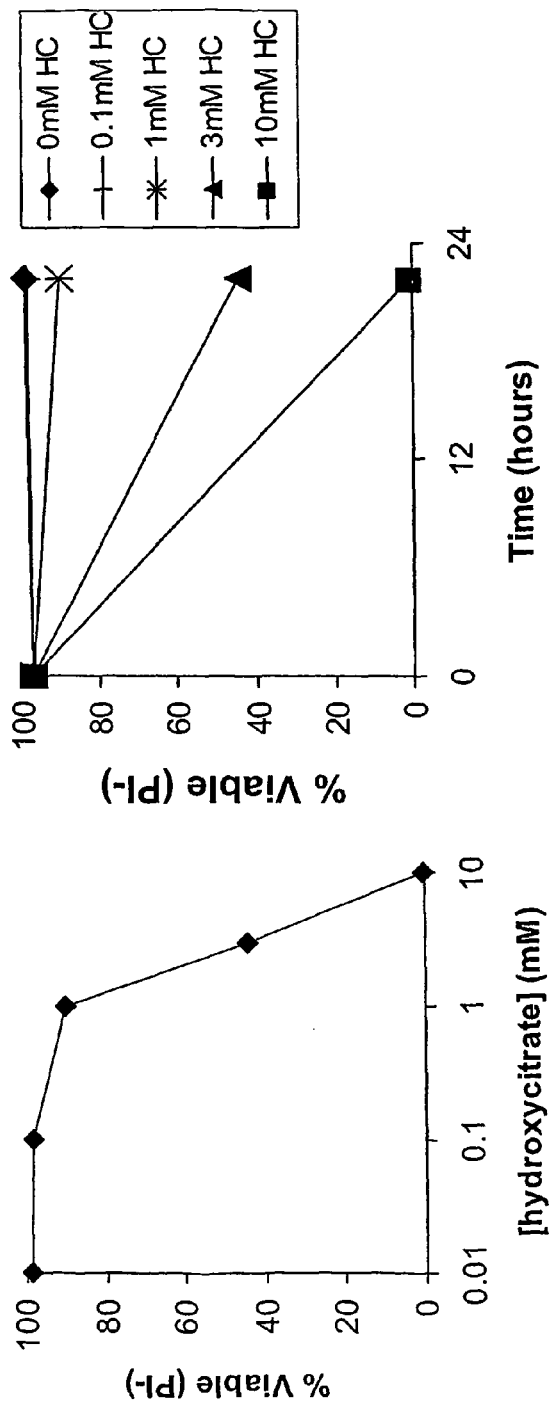

Previous studies have suggested that hydroxycitrate can act in cultured fat and liver cells as a competitive inhibitor of ATP citrate lyase activity (Berkhout, T. A., et al. Biochem J. 272: 181-186, 1990, which is incorporated herein by reference). As a result, we have investigated the ability of hydroxycitrate to inhibit the proliferative response of FL5.12 cells stimulated by interleukin-3. In FIG. 3, we demonstrate that the addition of hydroxycitrate to IL-3-containing cultures of FL5.12 leads to progressive decline in the overall cell number and viability of cells in cell culture (FIG. 3). The IC50 of this effect approximates the efficacy of hydroxycitrate in inhibiting ACL-dependent fatty acid synthesis as reported by others (Pearce et al. 1998). Together, these data argue that proliferating cells not only induce ATP citrate lyase activity in response to proliferation, but ACL activity is required for the continued proliferation and survival of growing mitogen-induced cell cultures.

Inhibition of Cell Proliferation and Cell Survival is a General Property of ATP Citrate Lyase Inhibitors.

Figure 6:
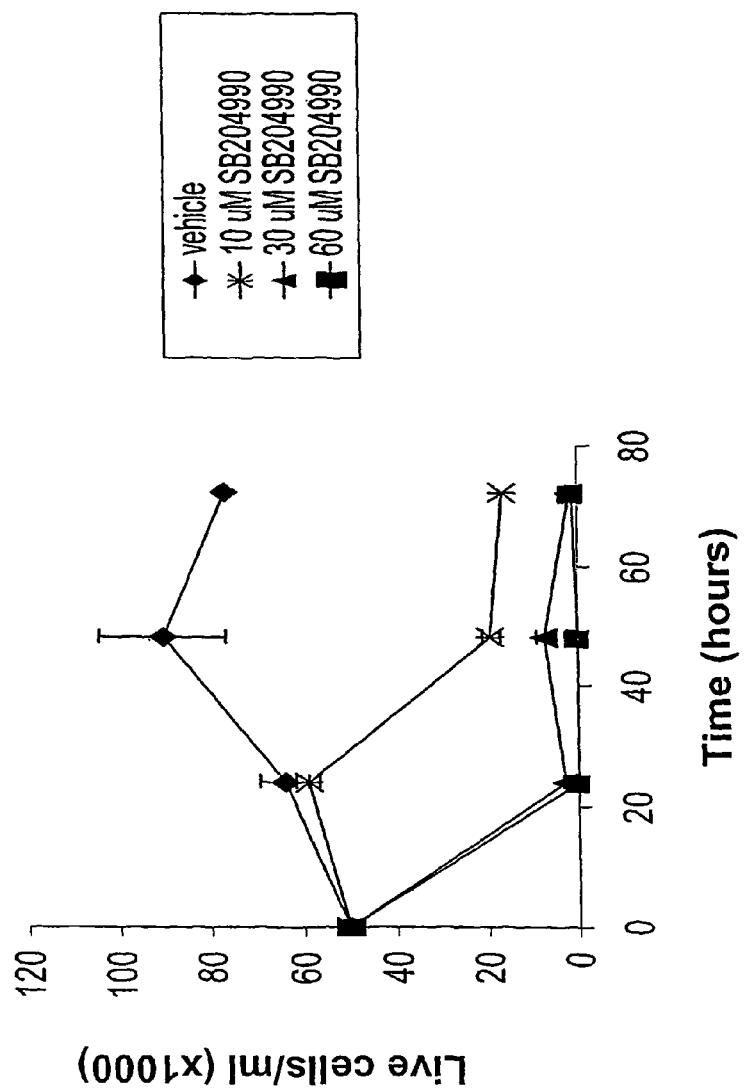
Figure 7:
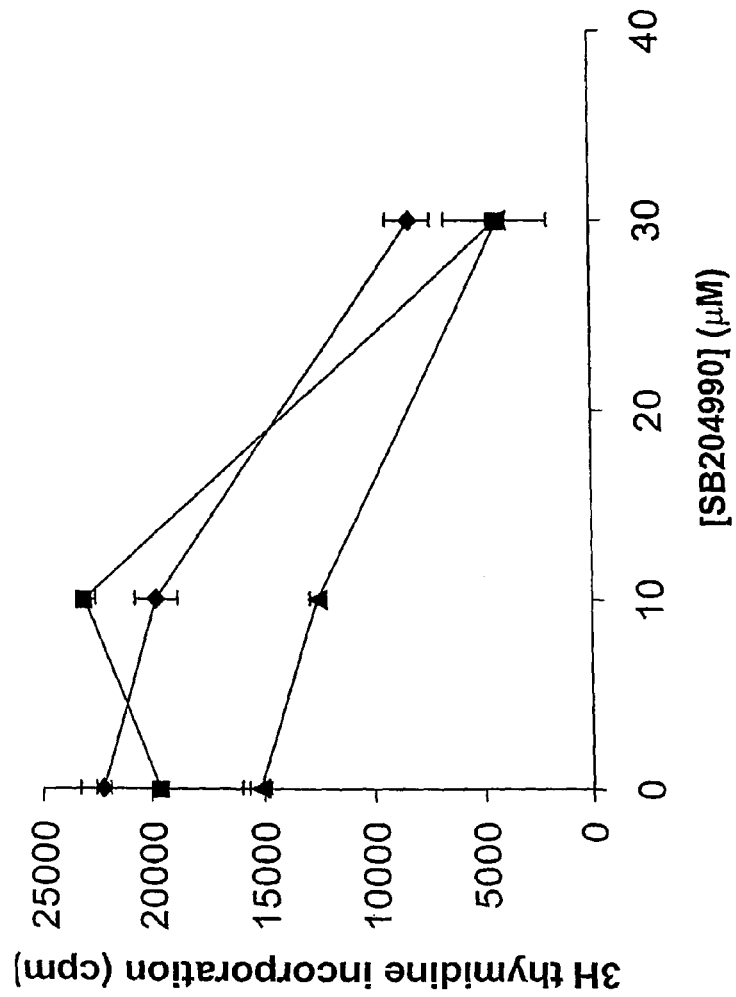
Figure 8:
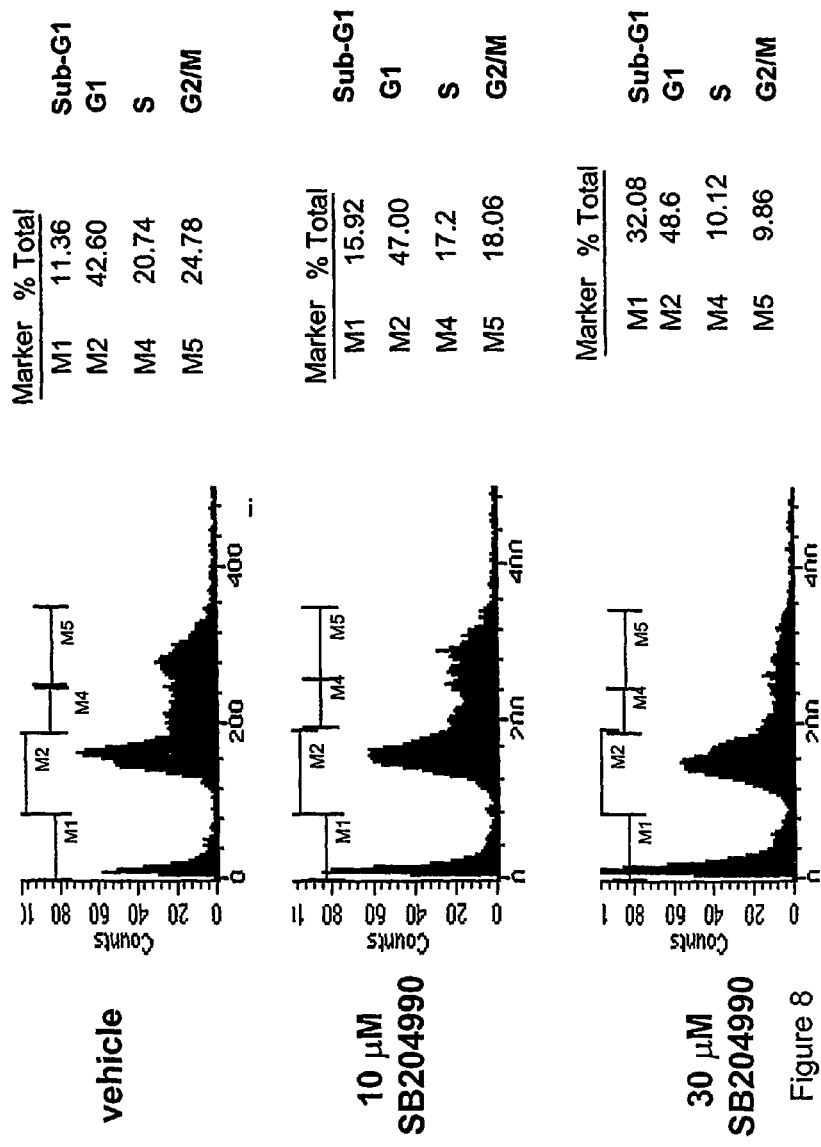
Figure 9:
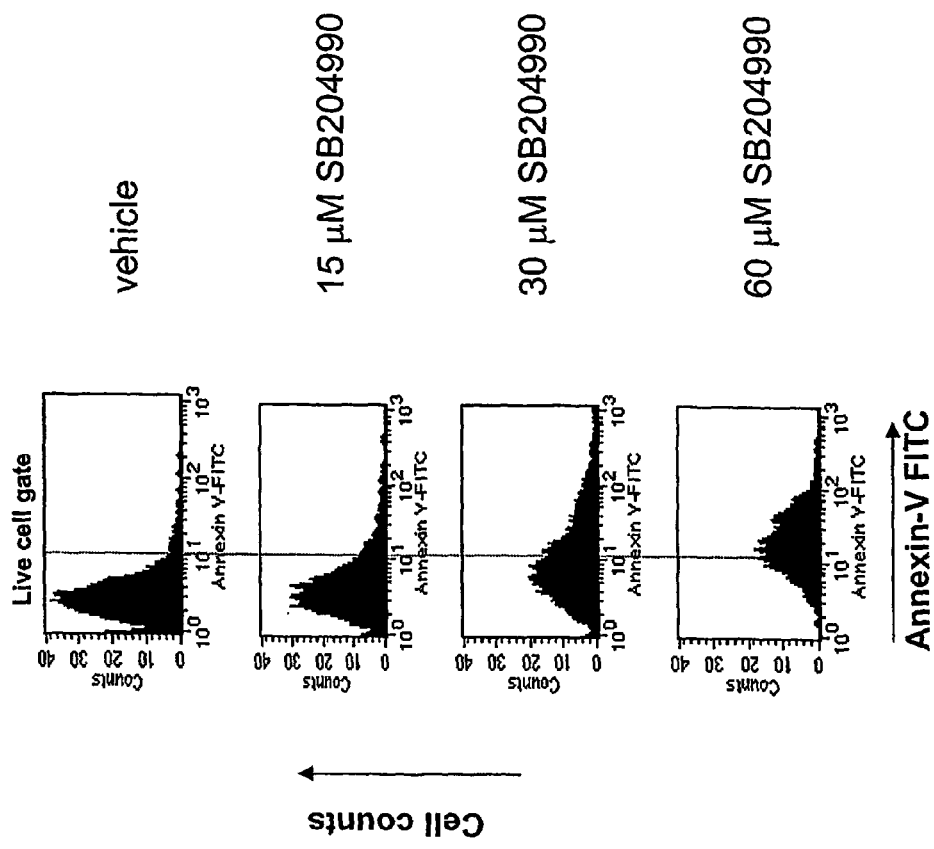

To investigate whether or not the effects of hydroxycitrate correspond to its demonstrated activity in inhibiting ATP citrate lyase activity and not promiscuous effects resulting from the relatively high concentrations necessary to induce inhibition of ACL activity and cell proliferation and apoptosis, we have confirmed the results secondarily with a series of compounds recently reported to act as ATP citrate lyase inhibitors (FIG. 4) In contrast to hydroxycitrate, these compounds act as micromolar inhibitors of ATP citrate lyase activity in cellular extracts. When 3-carbox-11-(2,4-dichlorophenyl)-3,5dihydroxyundecanoic acid (see FIG. 4 for structures) is added to mitogen stimulated cell extracts with an IC50 of approximately 3 µM and when cells were treated with a γ-lactone derivative that is cell permeant, the cell proliferation was inhibited at approximately a 10 µM concentration and both cell proliferation and cell survival were inhibited at 30 µM concentrations (FIG. 6). Reproducibility of the inhibition of cell proliferation in immortalized hematopoietic cells was investigated further by investigating independent cell clones which demonstrated that cell proliferation was inhibited approximately 50% in each clone at doses between 10 and 30 µM (FIG. 7). Treatment of cells with concentrations of 30 µM of the cell penetrant compound were associated with G1 arrest of rnitogen-stimulated cells and proliferating transformed cell cultures (FIG. 8) and the rapid induction of the annexin-V positivity (FIG. 9) demonstrative of the induction of apoptosis.

Oncogene Transformation Makes Cells More Sensitive to ACL Inhibition

Figure 10:
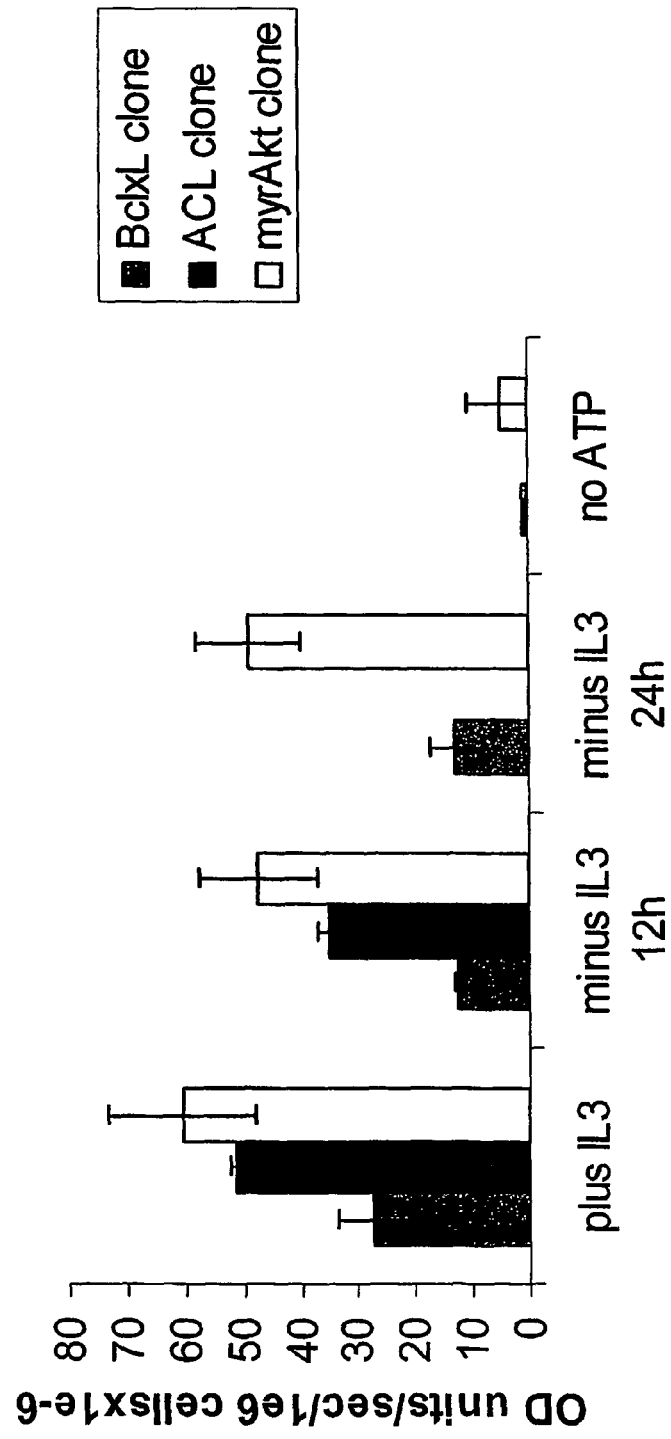
Figure 11:
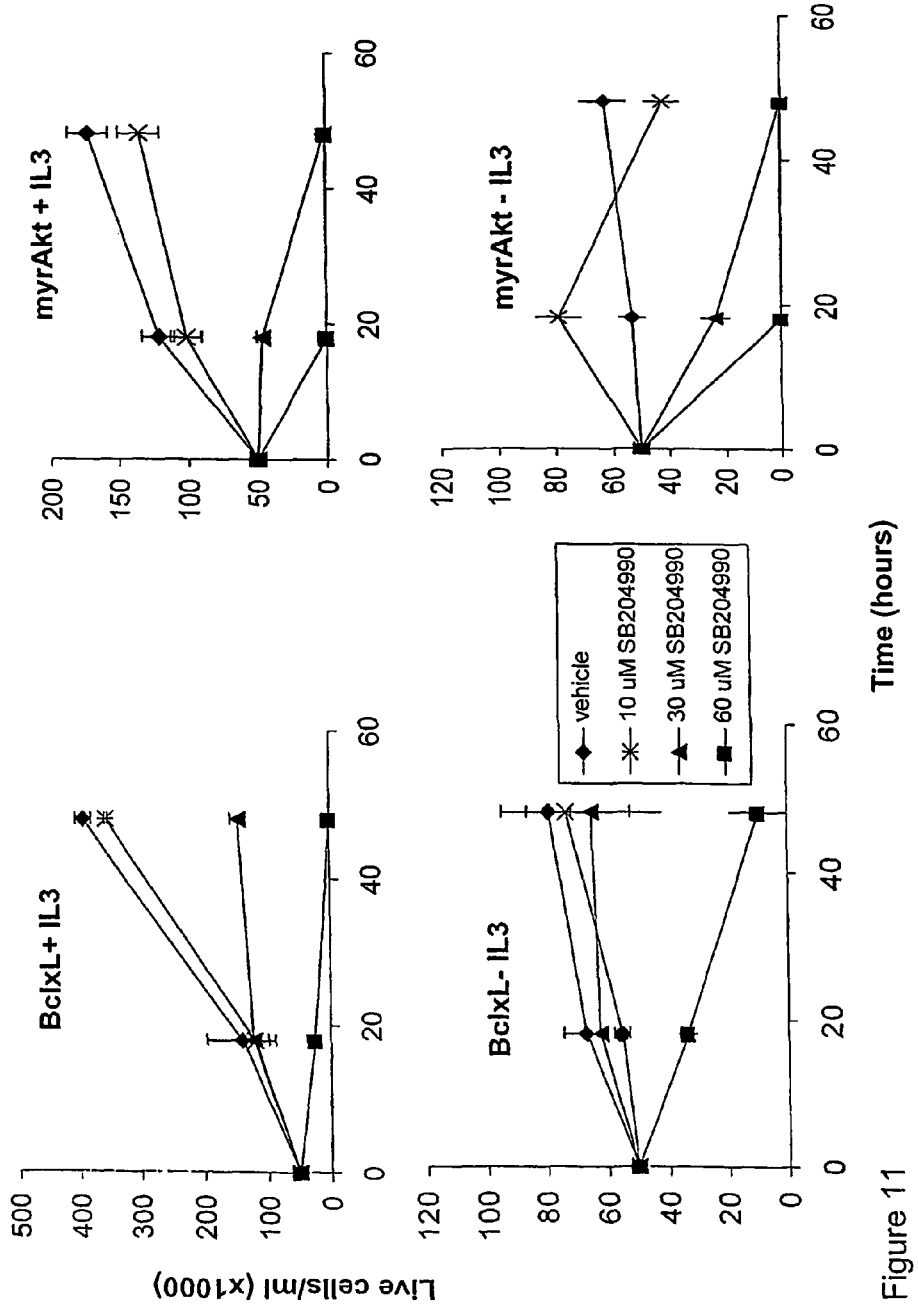

Previous work in our laboratory has demonstrated that cells transformed with either activated mutations of Akt or loss of the tumor suppressor function, PTEN, display a dramatic upregulation of their rate of glycolysis (Plas et al. 2001; Frauwirth et al. 2002). This is a feature demonstrated by many human malignancies as they progress to an invasive and metastatic phenotype and was originally described by Warburg et al. in 1929 and extensively confirmed more recently by the increasing clinical use of PET scanning using fluoro-deoxy-glucose. To determine whether transformation with Akt would increase further ATP citrate lyase activity, we made stable transfectants of the IL-3-dependent cell line, FL5.12, with a constitutively activated version of Akt produced by addition of a myristoylation site at the N-terminus. We found Akt-transformed cells when growing in the presences of IL-3 had even higher levels of ACL activity than those observed in ACL-transfected clones (FIG. 10). This is consistent with the recent report by others that ACL is a substrate of Akt phosphorylation (Berwick et al. 2002) and that Akt may be one molecular mechanism for the post-translational activation of ACL activity. Furthermore, in contrast to ACL- and Bcl-$x_L$-transfected clones, clones transfected with myristdylated Akt are resistant to the decline in ACL activity that normally accompanies withdrawal from the cell cycle. Akt transformed cells, even in a non-proliferating state, maintain a high rate of glycolysis. To determine whether this continues to render them sensitive to ACL inhibition even in the absence of a proliferative response we have investigated the sensitivity of myristoylated Akt cells to ACL inhibition in the presence or absence of the mitogen IL-3 (FIG. 11). Myristoylated Akt-transfected cells display no difference in their IC50 to ACL inhibition as measured by cell survival whether the cells were growing in the presence of IL-3 or had arrested in the G0/G1 phase of the cell cycle as a response to IL-3 withdrawal. In contrast, cells transfected with the oncogene Bcl-$x_L$ which does not increase ACL activity and which display a decline in ACL activity upon growth factor withdrawal, display a considerable difference in the susceptibility to cell death upon inhibition of ACL in the presence or absence of the mitogen IL-3. At 30 µM of the γ-lactone inhibitor of ATP citrate lyase there is near complete inhibition of mitogen-induced cell proliferation and there is the induction of apoptotic cell death. In contrast, 30 µM of the same compound in nongrowing cells is relatively nontoxic. This suggests that oncogene transformation of cells by addition of oncogenes that activate glycolysis leads to further enhanced susceptibility of transformed cells to ACL activation. Furthermore, this sensitivity to activation is independent of the cell cycle.

Human Tumor Cells are Sensitive to ACL Inhibition.

Figure 12A:
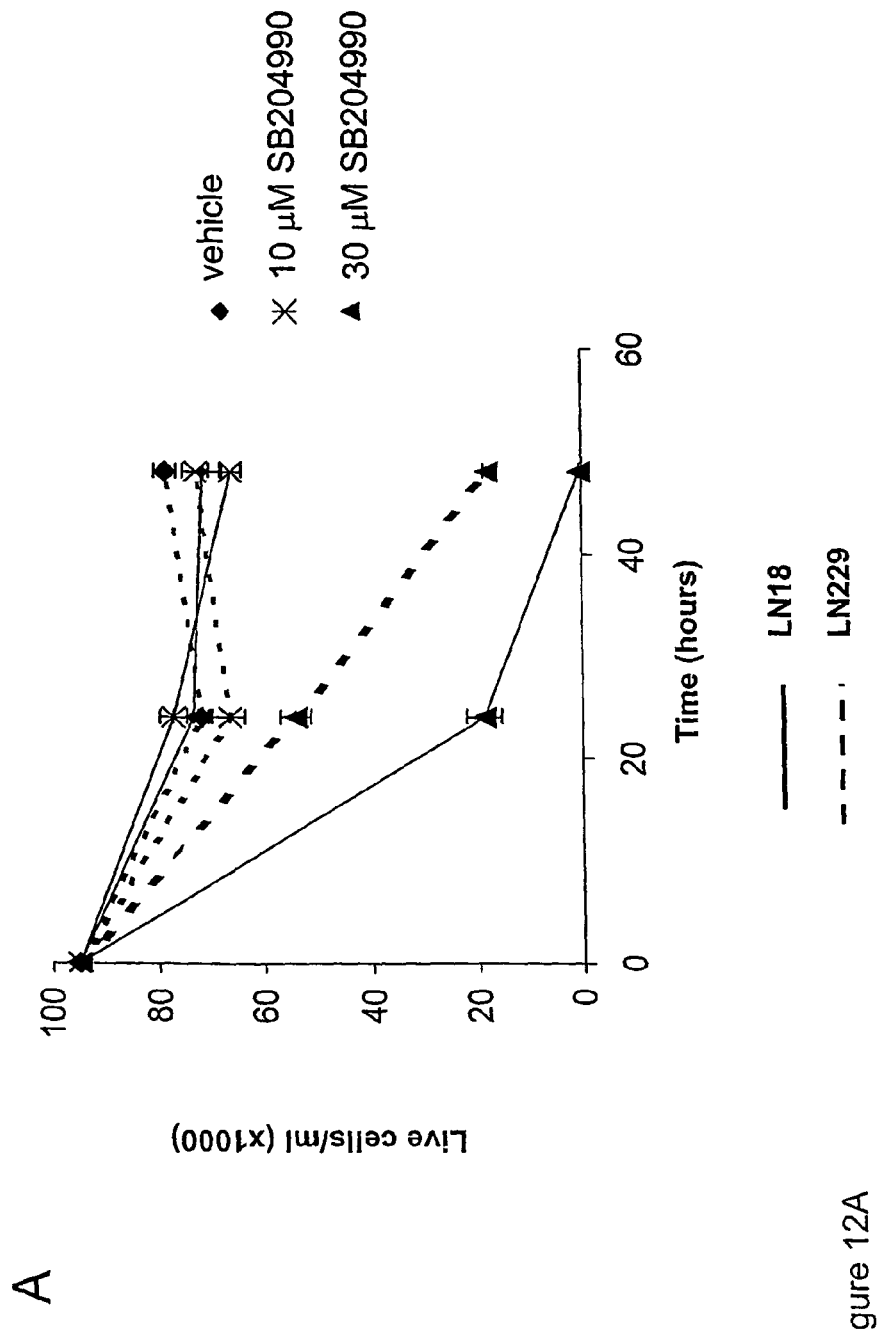
Figure 12B:
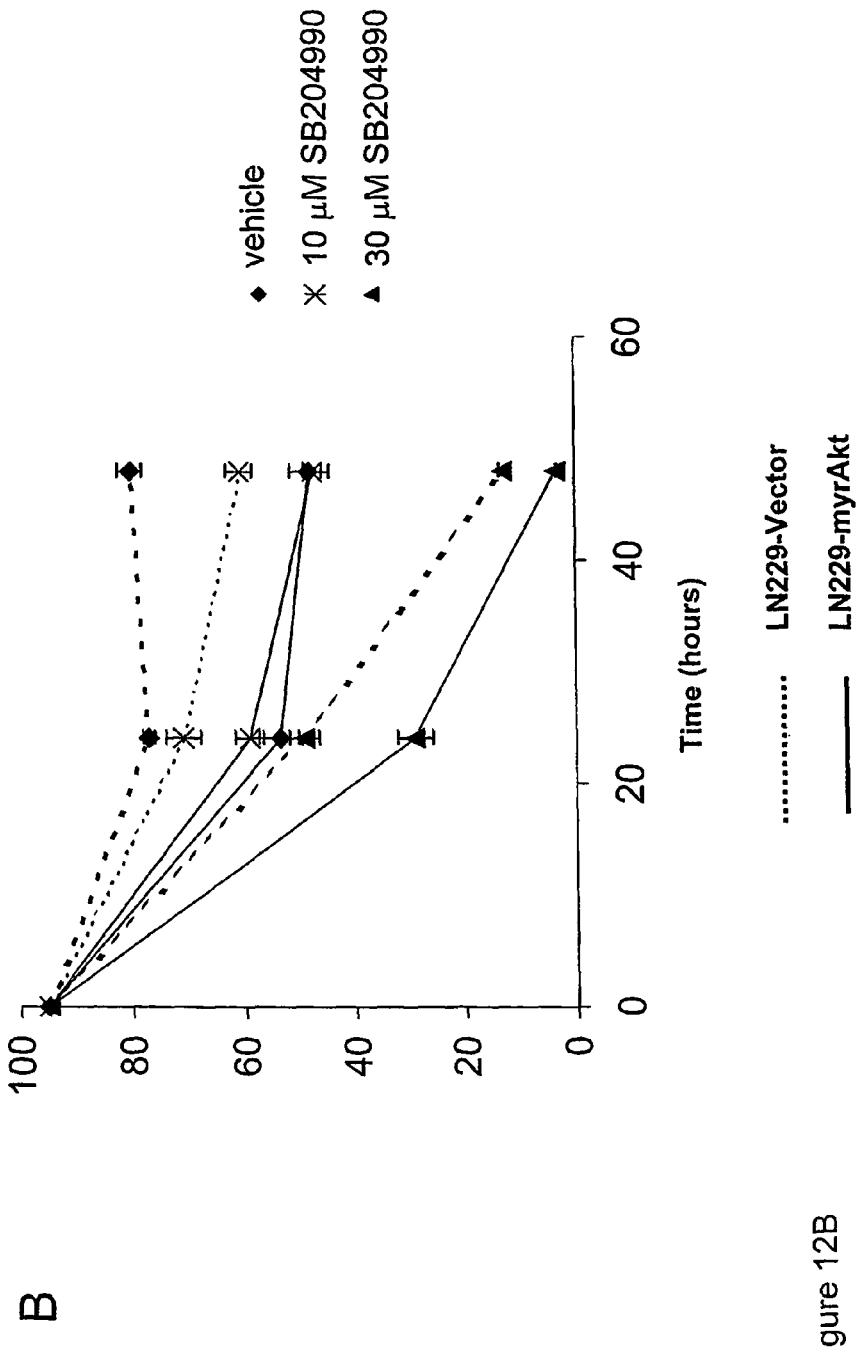

To validate our results in primary human tumor-derived cell lines, we have analyzed glioblastoma cell lines isolated from patients (FIG. 12). Two such glioblastoma cell lines are LN18 and LN229. Although these two tumors display similar growth rates in culture and in vivo, LN18 appears to have a constitutively active form of Akt while LN229 activates Akt only in response to mitogen stimulation. When growing in the absence of serum, both of the proliferating cell cultures exhibit a dose-dependent arrest of cell accumulation and the inhibition of cell survival in response to inhibitors of ATP citrate lyase. As for the Akt transformed cell lines, glioblastoma LN18 which has an activated Akt, demonstrates increased susceptibility. To determine whether this correlates with Akt activity, LN229 glioblastoma cells were transfected with a constitutively form of Akt and retested for their sensitivity to inhibition of ATP citrate lyase. LN229 cells transfected with myristoylated Akt in comparison to the cells transfected with the vector alone displayed increased sensitivity to undergoing apoptosis in response to ATP citrate lyase inhibition. These data confirm that human tumors display sensitivity to undergoing cell growth arrest and apoptosis in response to ATP citrate lyase inhibition and that this sensitivity can be further enhanced by oncogenes that stimulate the aerobic glycolysis of such cells.

Vegetative Cells are Less Sensitive than Proliferating Cells to Treatment of the ATP Citrate Lyase Inhibitors.

Figure 13:
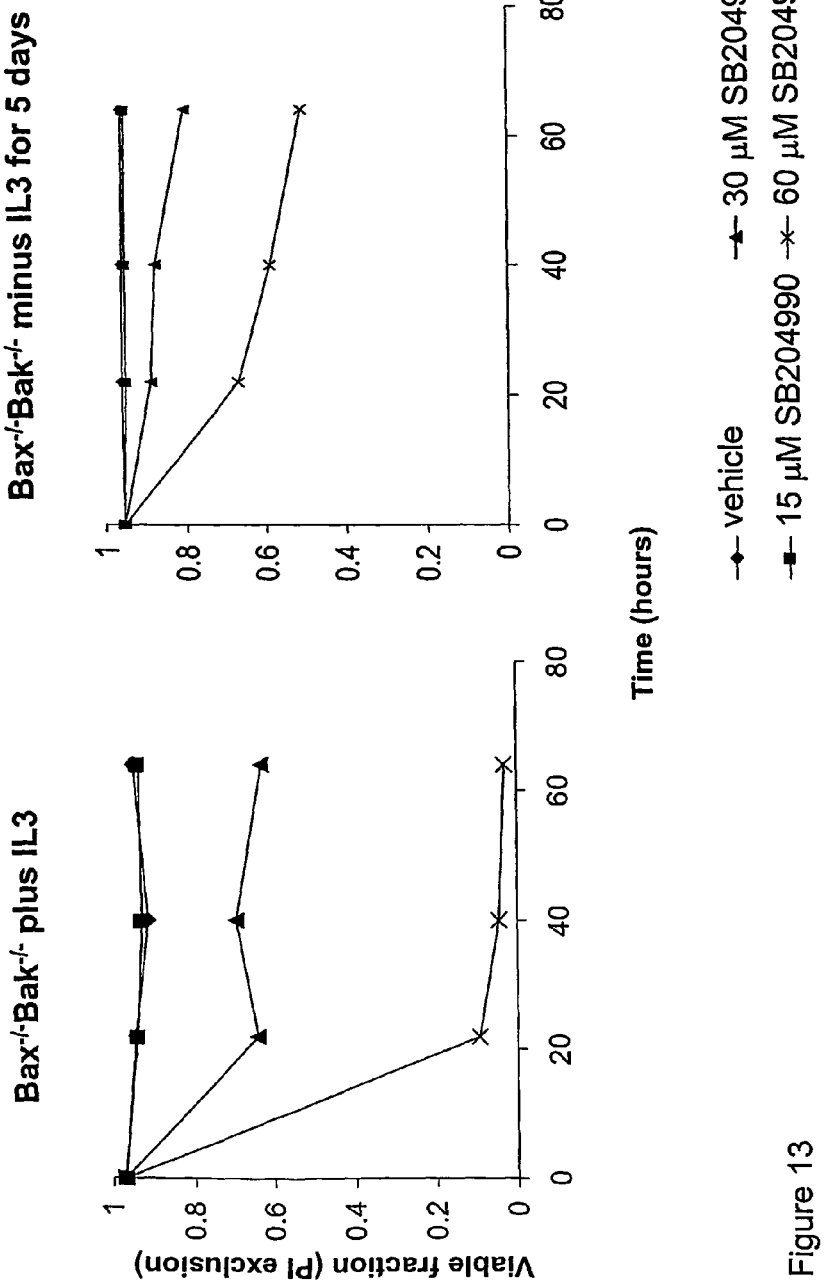
Figure 14A:
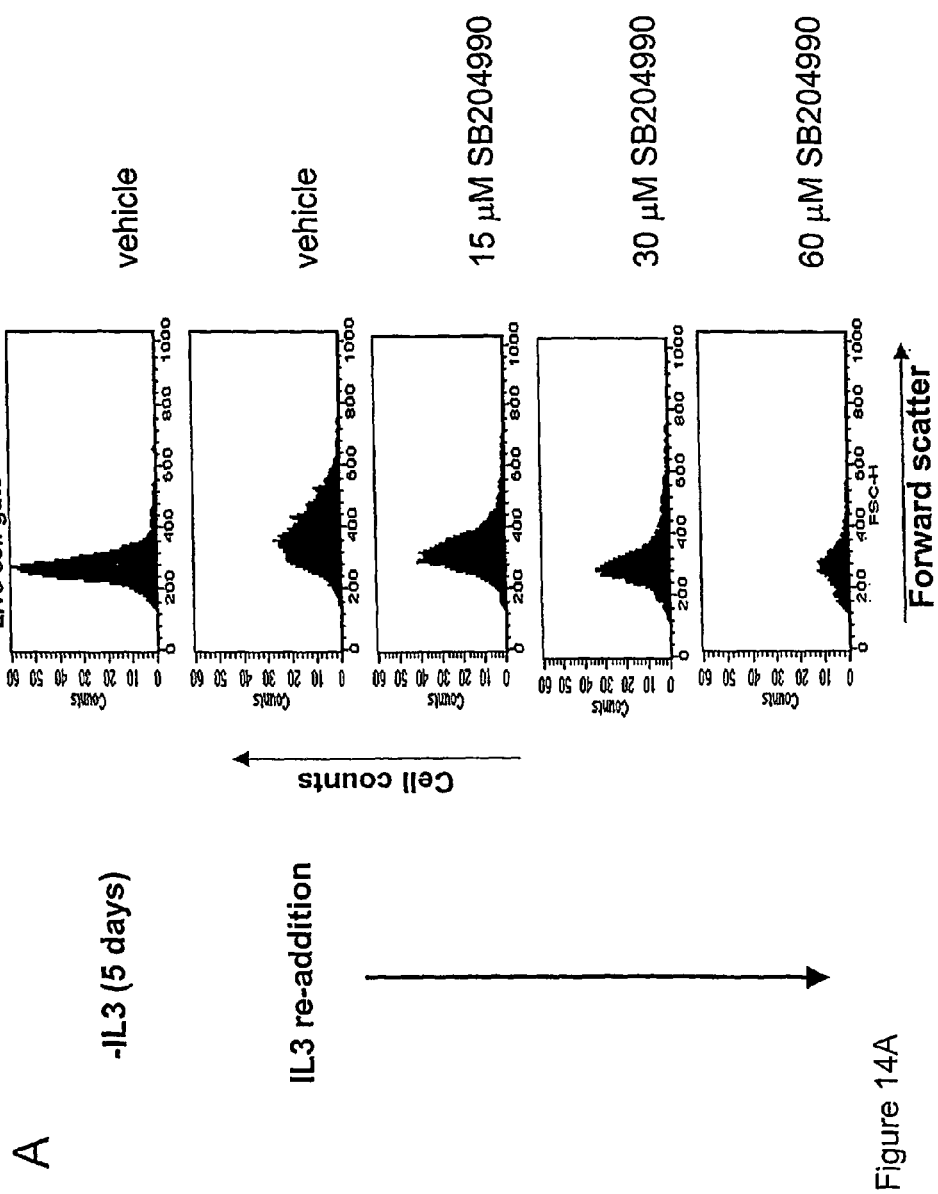
Figure 14B:
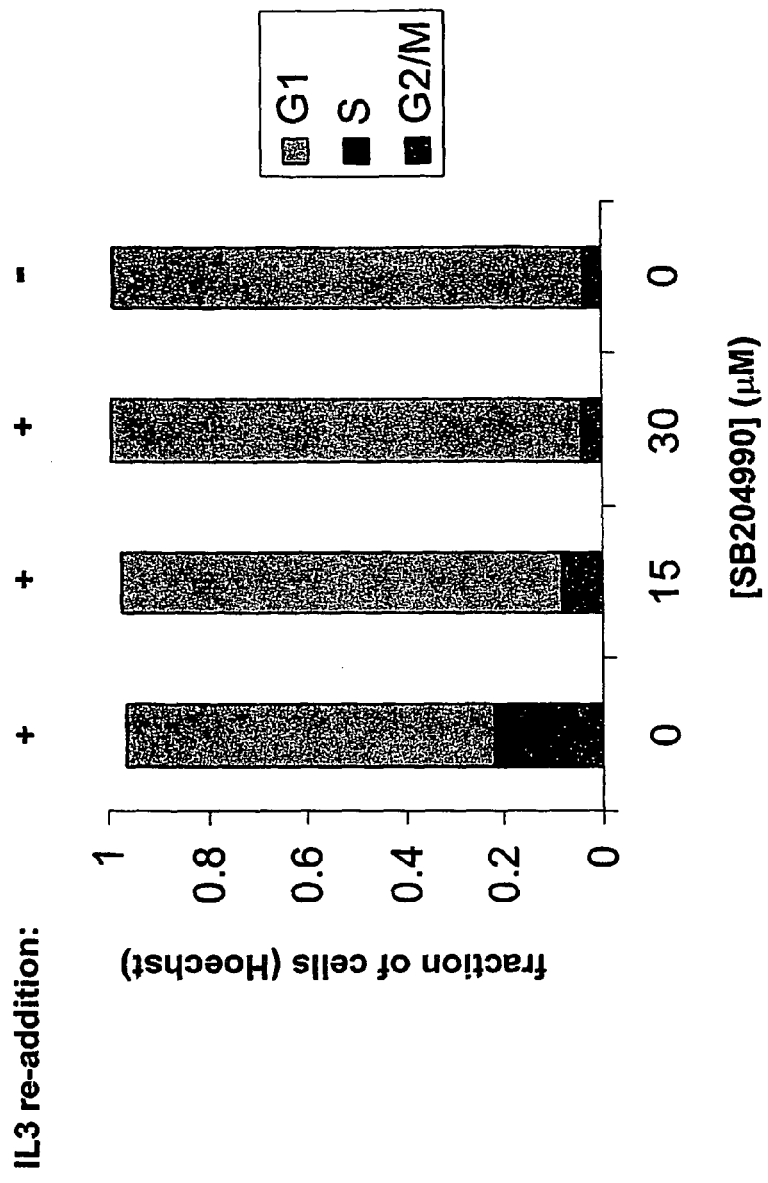
Figure 15:
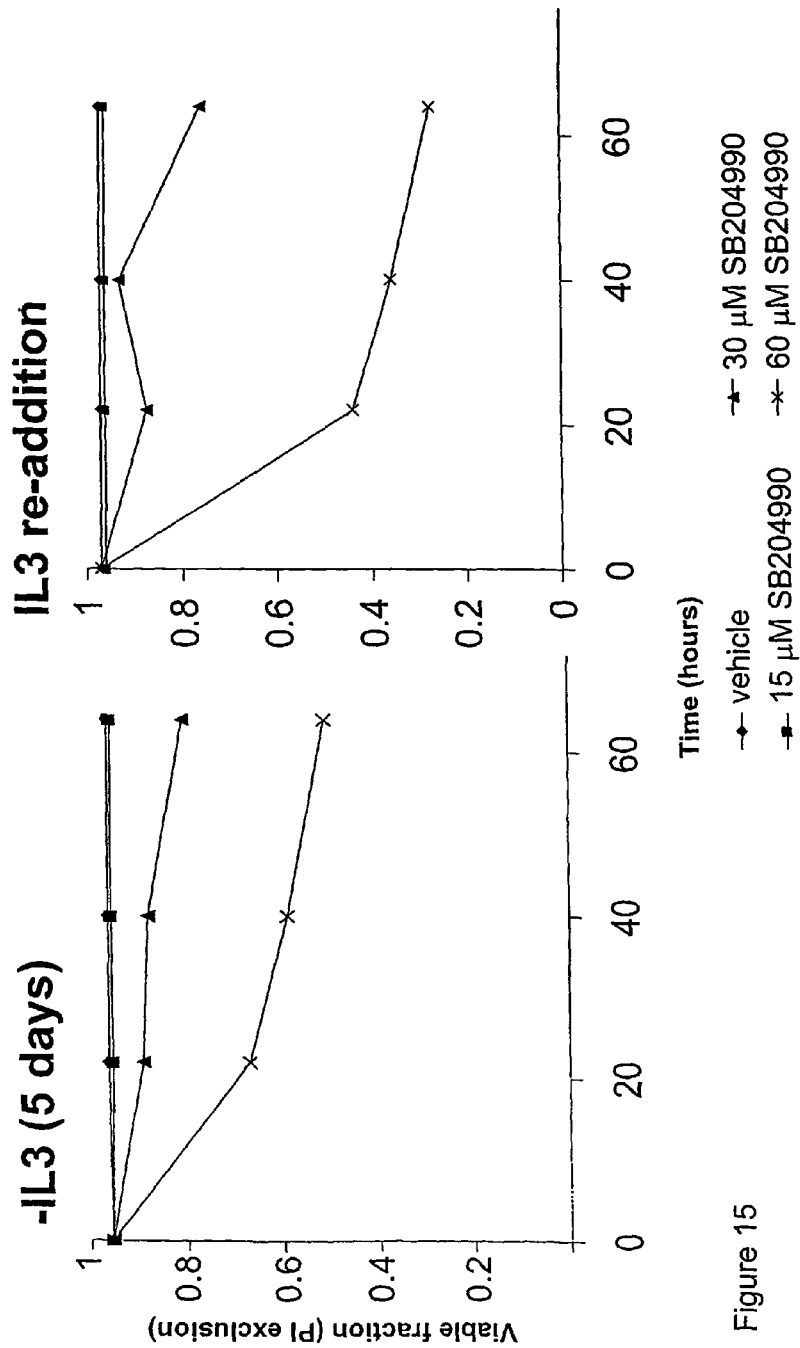

The vast majority of cells in humans are in a vegetative or nonproliferating state. For a cancer treatment to have a therapeutic window, it is important that the drug have greater effects on the proliferating clone or transformed cells than on nonproliferating cells. To address these issues in an in vitro culture system, we have taken advantage of the availability of mitogen-dependent cell lines in which apoptosis has been rendered deficient by the deletion of the proapoptotic molecules Bax and Bak. In the presence of IL-3, these cell lines grow continuously in culture but upon IL-3 deprivation the cells withdraw from the cell cycle but survive in a vegetative state for weeks. To determine whether or not cell proliferation increases the sensitivity of the cells to ATP citrate lyase inhibition, we have treated Bax/Bak-deficient, IL-3-dependent cell lines with ATP citrate lyase inhibitors when growing in the presence of IL-3 (FIG. 13). Cell growth in response to IL-3 dramatically increased the sensitivity of the cells to ACL inhibition. These cells also allowed us to secondarily test the effects of ATP citrate lyase inhibition on cell growth. Resting Bax/Bak-deficient cells were treated with IL-3 to induce their growth and re-entry into the cell cycle. We were able to demonstrate that ATP citrate lyase inhibitors in a dose-dependent fashion inhibited mitogen-induced cell growth in a dose-dependent fashion. At a dose of 30 µM SB20499 nearly completely inhibited the mitogen-induced cell growth of these cells lines (FIG. 14). Furthermore, we were able to demonstrate that mitogenic stimulation rendered quiescent cells more sensitive to the effects of ATP citrate lyase inhibitor when compared to their vegetative counterparts. Vegetative cells treated with mitogens become selectively more sensitive to treatment of ATP citrate lyase inhibitors as measured by cell survival (FIG. 15). Together, these data suggest that transformed cells display a high rate of aerobic glycolysis and display a high sensitivity to inhibition of ATP citrate lyase as manifested by inhibition of cell proliferation of the induction of apoptotic cell death. In addition, nonproliferating cells are relatively resistant to the effects of such inhibitors and nontransformed cells display intermediate sensitivity, suggesting that there is a therapeutic window for efficacy of ATP citrate lyase inhibitors in the treatment of cancer.

Mechanism of Action of ATP Citrate Lyase Inhibitors.

Figure 16:
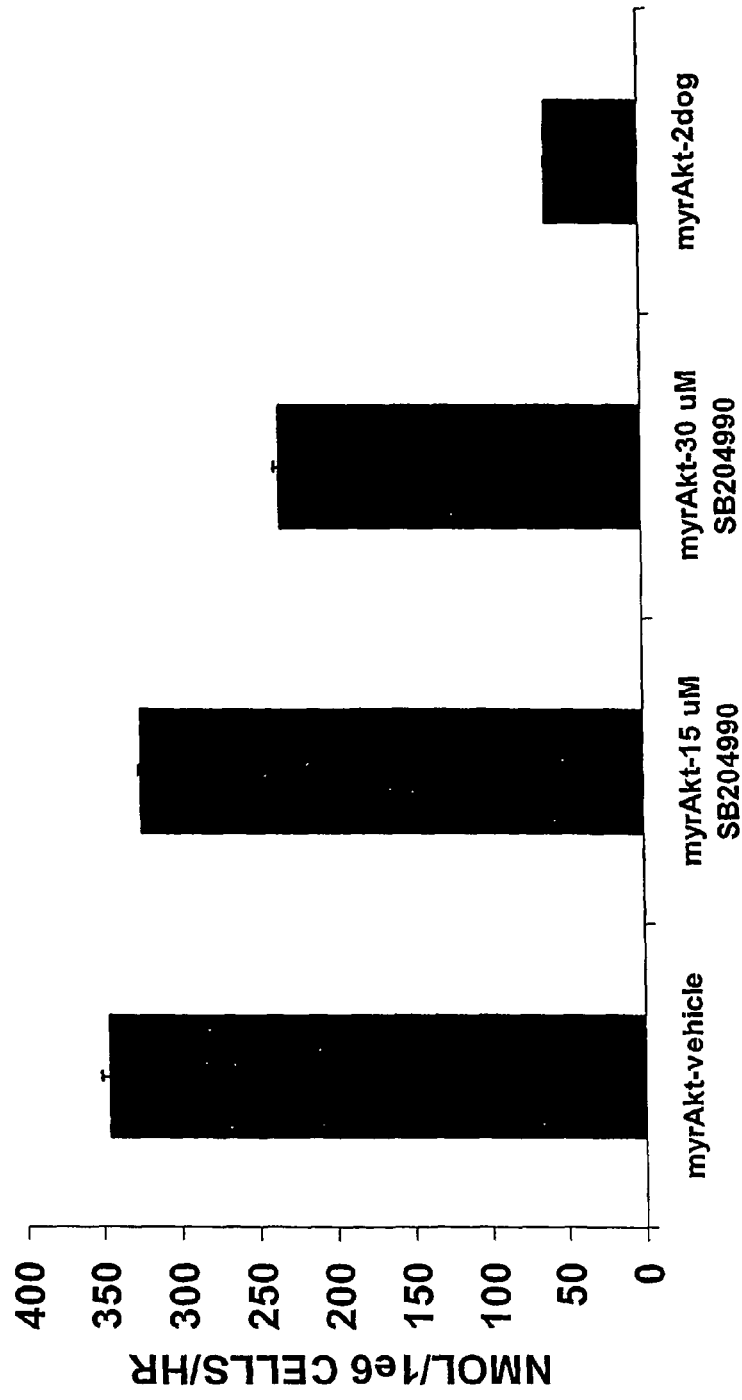

To further determine the molecular basis of action of ATP citrate lyase inhibitors, additional studies were undertaken. We have previously demonstrated that Akt-transformed cells become dependent on a high rate of glycolytic metabolism to maintain their proliferation and cell survival. One expected effect of ATP citrate lyase inhibition is the build-up of citrate in the cytosol, which can act as a negative allosteric regulator of the glycolytic pathway. To test whether or not treatment with ATP citrate lyase inhibitors can lead to inhibition of the glycolytic rate of Akt-transformed cells, we have tested whether or not brief treatments with an ACL inhibitor can suppress the glycolytic rate of Akt-transformed cells in a dose-dependent fashion (FIG. 16). In transformed cells displaying a high rate of aerobic glycolysis, the inhibition of ATP citrate lyase and the build-up of citrate in the cytosol may prevent these cells from maintaining their bioenergics through a high rate of glycolysis and thus result in selectively toxicity.

Figure 17:
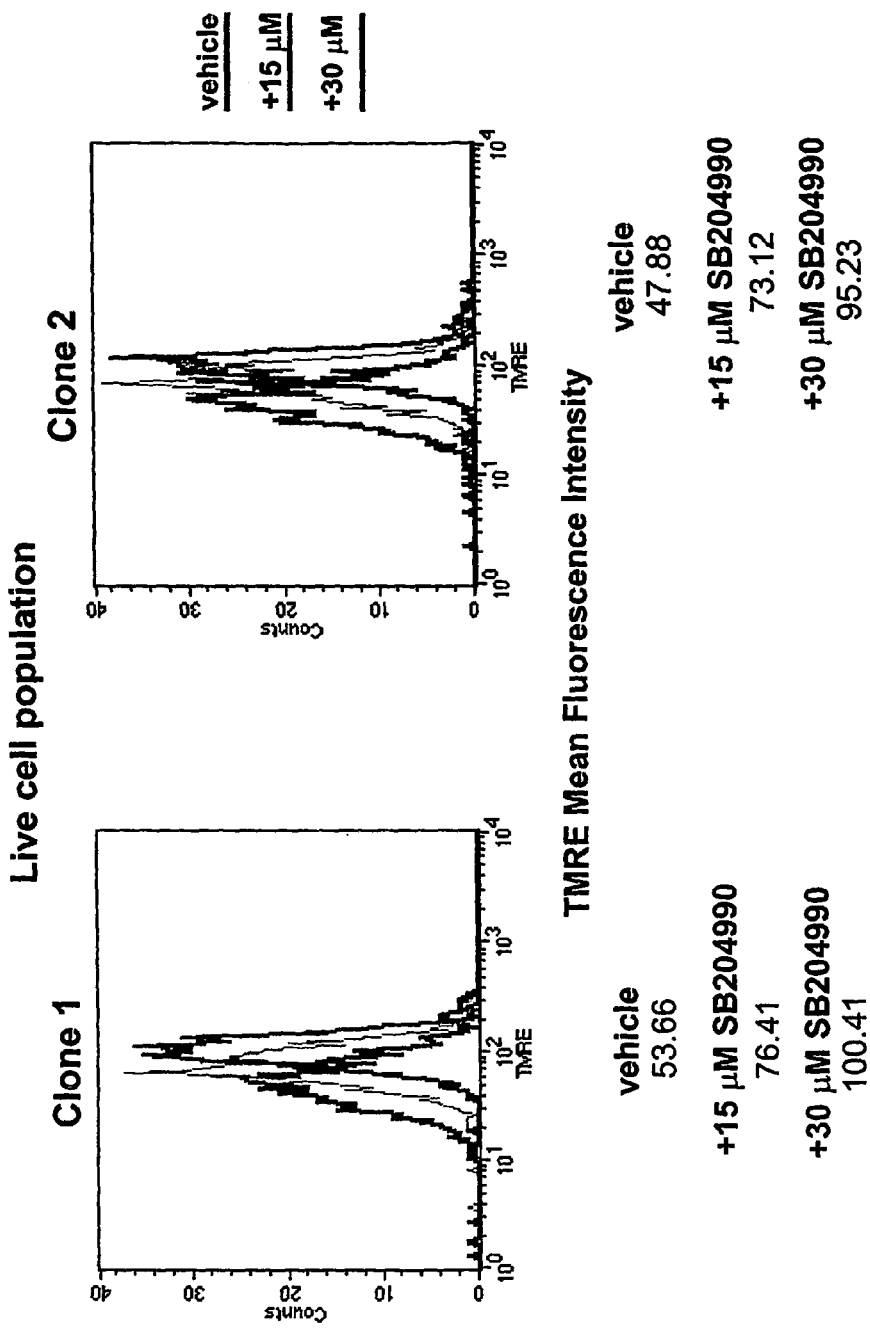
Figure 18:
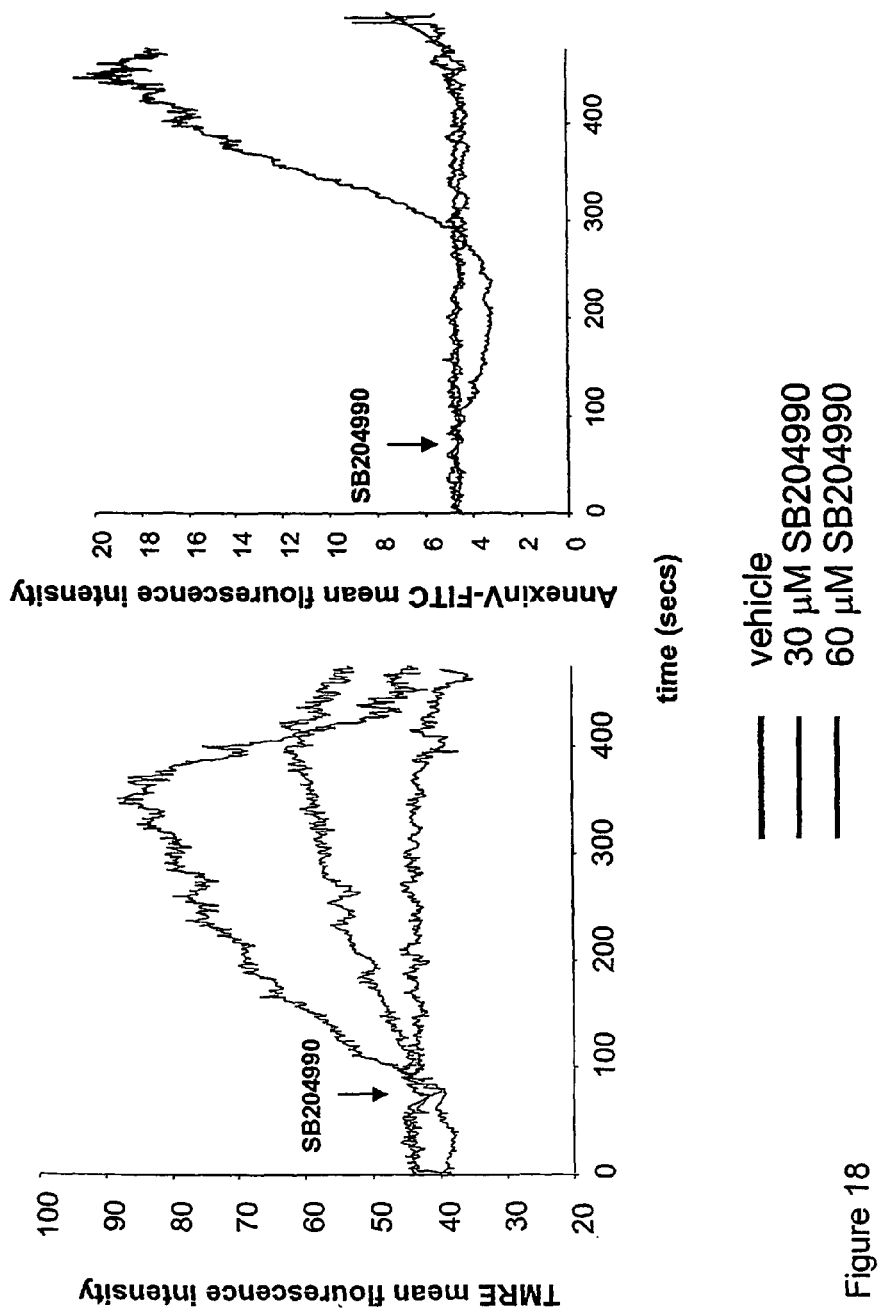

A secondary consequence of ATP citrate lyase inhibition would be that citrate could no longer be consumed in the cytosol and therefore would build up in the mitochondrial matrix, providing an increased substrate availability to the TCA cycle and thus increasing the production of NADH and the activity of the electron transport chain. Consistent with this we have measured the mitochondrial potential in cells treated with increasing doses of ATP citrate lyase inhibitors and found that there is a dose-dependent increase in the mitochondrial membrane potential (FIG. 17). We have previously published that persistent hyperpolarization of mitochondria can lead to apoptosis through mitochondrial swelling and lipid membrane peroxidation (Vander Heiden et al. 1997). To determine whether this mitochondrial hyperpolarization precedes the induction of apoptosis in cells, we have tested the time course of mitochondrial hyperpolarization in annexin-V positivity in cells transfected with an oncogenic form of Akt. As noted in the previous figure, addition of ATP citrate lyase inhibitors leads to a dose-dependent increase in mitochondrial membrane potential. Immediately following the maximum induction of mitochondrial hyperpolarization there is a decline in mitochondrial potential followed by the induction of annexin-V positivity indicative of initiation of apoptotic cell death (FIG. 18). Thus, inhibition of glycolytic stimulation and mitochondrial hyperpolarization appear to predispose treated cells to the induction of apoptosis.

Conclusions

The above data suggest that cancer cells display a selective sensitivity to ATP citrate lyase inhibitors through mechanism-based effects on the regulation of the glycolytic pathway, mitochondrial physiology, and the requirement for the products of ATP citrate lyase activity in cellular growth. Furthermore, sensitivity to ATP citrate lyase inhibition is much greater in proliferating cells than in nonproliferating cells and is dramatically enhanced in cells that have undergone oncogenic transformation that leads to the induction of aerobic glycolysis. We therefore propose the use of ATP citrate lyase inhibitors in the treatment of cancer and suggest that it will be particularly efficacious in cells transformed through activation of Akt or deletion of PTEN, cells that display an enhanced rate of aerobic glycolysis as measured by PET scanning, and in cells growing at metastatic sites.

References, Which are Each Incorporated Herein by Reference:

1. Barth, C., Hackenschmidt, J., Ulmann, H., and Decker, K. Inhibition of cholesterol synthesis by (−)-hydroxycitrate in perfused rat liver. Evidence for an extramitochondrial mevalonate synthesis from acetyl coenzyme A. FEBS Lett, 22: 343-346, 1972.
2. Benjamin, W. B., Pentyala, S. N., Woodgett, J. R. Hod, Y., and Marshak, D. ATP citrate lyase and glycogen synthase kinase-3 beta in 3T3-L1 cells during differentiation into adipocytes. Biochem J, 300: 477-482, 1994.
3. Berkhout, T. A., Havekes, K. M., Pearce, N. J., and Groot, P. H. The effect of (−)-hydroxycitrate on the activity of the low-density-lipoprotein receptor and 3-hydroxy-3-methylglutaryl-CoA reductase levels in the human hepatoma cell line Hep G2. Biochem J. 272: 181-186, 1990.
4. Berwick, D. C., Hers, I., Heesom, K. J., Moule, S. K., and Tavare, J. M. The identification of ATP-citrate lyase as a protein kinase B (Akt) substrate in primary adipocytes. J Biol Chem, 277:33895-33900, 2002.
5. Dolle, R. E., McNair, D., Hughes, M. J., Kruse, L. I., Eggelston, D., Saxty, B. A., Wells, T. N., and Groot, P. H. ATP-citrate lyase as a target for hypolipidemic intervention. Sulfoximine and 3-hydroxy-beta-lactam containing analogues of citric acid as potential tight-binding inhibitors. J Med Chem, 35:4875-4884, 1992.
6. Dolle, R. E., Gribble, A., Wilkes, T., Kruse, L. I., Eggleston, D., Saxty, B. A., Wells, T. N., and Groot, P. H. Synthesis of novel thiol-containing citric acid analogues. Kinetic evaluation of these and other potential active-site-directed and mechanism-based inhibitors of ATP citrate lyase. J Med Chem, 38: 537-543, 1995.
7. Elshourbagy, N. A., Near, J. C., Kmetz, P. J., Sathe, G. M., Southan, C., Strickler, J. E., Gross, M., Young, J. F., Wells, T. N., and Groot, P. H. Rat ATP citrate lyase. Molecular cloning and sequence analysis of a full-length CDNA and MRNA abundance as a function of diet, organ, and age. J Biol Chem, 265: 1430-1435, 1990.
8. Elshourbagy, N. A., Near, J. C. Kmetz, P. J., Wells, T. N., Groot, P. H., Saxty, B. A., Hughes, S. A., Franklin, M., and 8. Gloger, I. S. Cloning and expression of a human ATP-citrate lyase cDNA. Eur J Biochem, 204: 491-499, 1992.
9. Fang, M. and Lowenstein, J. M. Citrate and the conversion of carbohydrate into fat. The regulation of fatty acid synthesis by rat liver extracts. Biochem J, 105: 803:811, 1967.
10. Frauwirth, K. A., Riley, J. L., Harris, M. H., Parry, R. V. Rathmell, J. C., Plas, D. R., Elstrom, R. L., June, C. H., and Thompson, C. B. The CD28 signaling pathway regulates glucose metabolism. Immunity, 16:769-777, 2002.
11. Fukuda, H. and Iritani, N. Regulation of ATP citrate lyase gene expression in hepatocytes and adipocytes in normal and genetically obese rats. J Biochem (Tokyo), 126: 437-444, 1999.
12. Gribble, A. D., Doll, R. E., Shaw, A., McNair, D., Novelli, R., Novelli, C. E., Slingsby, B. P., Shah, V. P., Tew, D., Saxty, B. A., Allen, M., Groot, P. H., Pearce, N., and Yates, J. ATP-citrate lyase as a target for hypolipidemic intervention. Design and synthesis of 2-substituted butanedioic acids as novel, potent inhibitors of the enzyme. J Med Chem, 39:3569-3584, 1996.
13. Gribble, A. D., Ife, R. J., Shaw, A., McNair, D., Novelli, C. E., Bakewell, S., Shah, V. P., Dolle, R. E., Groot, P. H., Pearce, N., Yates, J., Tew, D., Boyd, H., Ashman, S., Eggleston, D. S., Haltiwanger, R. C., and Okafo, G. ATP-Citrate lyase as a target for hypolipidemic intervention. 2. Synthesis and evaluation of (3R,5S)-omega-substituted-3-carboxy-3,5-dihydroxyalkanoic acids and their gamma-lactone prodrugs as inhibitors of the enzyme in vitro and in vivo. J Med Chem, 41:3582-3595, 1998.
14. Inoue, J., Suzuki, F., Fukunishi, K., Adachi, K., and Takeda, Y. Studies on ATP citrate lyase of rat liver. J Biol Chem, 60:543-553, 1966.
15. Lowenstein, J. M. Effect of (−)-hydroxycitrate on fatty acid synthesis by rat liver in vivo. J Biol Chem, 246:629-632, 1971.
16. Morikawa, J., Nishimura, Y., Uchida, A., and Tanaka, T. Molecular cloning of novel mouse and human putative citrate lyase beta-subunit. Biochem Biophys Res Commun, 289:1282-1286, 2001.
17. Pearce, N. J., Yates, J. W., Berkhout, T. A., Jackson, B., Tew, D., Boyd, H., Camilleri, P., Sweeney, P., Gribble, A. D., Shaw, A., and Groot, P. H. The role of ATP citrate lyase in the metabolic regulation of plasma lipids. Hypolipidaemic effects of SB-204990, a lactone prodrug of the potent ATP citrate lyase inhibitor SB-201076. Biochem J, 334: 113-119, 1998.
18. Plas, D. R., Talapatra, S., Edinger, A. L., Rathmell, J. C., and Thompson, C. B. Akt and Bcl-$x_L$ promote growth factor-independent survival through distinct effects on mitochondrial physiology. J Biol Chem, 276:12041-12048, 2001.
19. Saxty, B. A., Novelli, R., Dolle, R. E., Kruse, L. I., Reid, D. G. Camilleri, P., and Wells, T. N. Synthesis and evaluation of (+) and (−)-2,2-difluorocitrate as inhibitors of rat-liver ATP-citrate lyase and porcine-heart aconitase. Eur J Biochem, 202: 889-896, 1991.
20. Sullivan, A. C., Triscari, J., Hamilton, J. G., Miller, O. N., and Wheatley, V. R. Effect of (−)-hydroxycitrate upon the accumulation of lipid in the rat. I. Lipogenesis. Lipids, 9:121-128, 1974.
21. Sullivan, A. C., Triscari, J., Hamilton, J. G., and Miller, O. N. Effect of (−)-hydroxycitrate upon the accumulation of lipid in the rat. II. Appetite. Lipids, 9: 129-134, 1974.
22. Sullivan, A. C., Dairman, W., and Triscari, J. (−)-threo-Chlorocitric acid: a novel anorectic agent. Pharmacol Biochem Behav, 15: 303-310, 1981.
23. Vander Heiden, M. G., Chandel, N. S., Williamson, E. K., Schumacker, P. T., and Thompson, C. B. Bcl-$x_L$ regulates the membrane potential and volume homeostasis of mitochondria Cell, 91:627-637, 1997.
24. Vander Heiden, M. G., Plas, D. R., Rathmell, J. C., Fox, C. J., Harris, M. H., and Thompson, C. B. Growth factors can influence cell growth and survival through effects on glucose metabolism. Mol Cell Biol, 21:5899-5912, 2001.
25. Watson, J. A. and Lowenstein, J. M. Citrate and the conversion of carbohydrate into fat. Fatty acid synthesis by a combination of cytoplasm and mitochondria J Biol Chem, 245: 5993-6002, 1970.

Example 3

The National Cancer Institute alphabetical list of cancer includes: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer, Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor, Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor, Glioma, Childhood Brain Stem; Glioma, Childhood Visual pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver, Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy, Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenström's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer, Nasopharyngeal Cancer, Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer, Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer, Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual pathway and Hypothalamic Glioma, Childhood; Vulvar Cancer; Waldenström's Macroglobulinemia; and Wilms' Tumor. The methods of the present invention may be useful to treat such types of cancer.

What is claimed is:

1. A method of treating an individual who has cancer that comprises cancer cells that have a high rate of aerobic glycolysis, the method comprising the steps of:
   identifying said cancer as a cancer that comprises cancer cells that have a high rate of aerobic glycolysis, wherein said cancer is determined to be a cancer that comprises cancer cells that have a high rate of aerobic glycolysis by PET imaging using $^{18}$fluoro-deoxyglucose, and subsequently
   administering to said individual a therapeutically effective amount of an ATP citrate lyase inhibitor, wherein said therapeutically effective amount of ATP citrate lyase inhibitor is sufficient to inhibit ATP citrate lyase activity in said cancer cells to result in inhibition of conversion of citrate into oxaloacetic and acetyl-CoA in said cancer cells, leading to hyperpolarization of mitochondria and increased reactive oxygen species production sufficient to cause said cell to undergo apoptosis
   wherein said cancer is selected from the group consisting of glioma, prostate cancer, bladder cancer, renal cancer and lung cancer.

2. The method of claim 1 comprising the step of administering to said individual a therapeutically effective amount of an ATP citrate lyase inhibitor; wherein said ATP citrate lyase inhibitor is (-)hydroxycitrate.

3. The method of claim 1, wherein said cancer comprises cancer cells that have a high rate of aerobic glycolysis and are not dependent on endogenously synthesized fatty acid, said method comprising the steps of:
   identifying said cancer as a cancer that comprises cancer cells that are not dependent on endogenously synthesized fatty acid and that have a high rate of aerobic glycolysis, and subsequently
   administering to said individual a therapeutically effective amount of an ATP citrate lyase inhibitor, wherein said therapeutically effective amount of ATP citrate lyase inhibitor is sufficient to inhibit ATP citrate lyase activity in said cancer cells to result in inhibition of conversion of citrate into oxaloacetic and acetyl-CoA in said cancer cells, leading to hyperpolarization of mitochondria and increased reactive oxygen species production sufficient to cause said cell to undergo apoptosis.

4. The method of claim 1 comprising the step of administering to said individual a therapeutically effective amount of a tricarboxylate transporter inhibitor; wherein said tricarboxylate transporter inhibitor is selected from the group consisting of: 1,2,3-benzenetricarboxylate, isocitrate, malate, phosphoenolpyruvate, n-butylmalonate, sulfhydryl reagents, diethyl pyrocarbonate, 2,3-butanedione, phenylglyoxal, pyridoxal, 5phosphate dicarboxylates, succinate, malate, oxaloacetate, tricarboxylates isocitrate, tricarballylate and palmitoyl-CoA.

5. The method of claim 1 comprising the step of further administering to said individual a different anti-cancer compound.

6. The method of claim 1 comprising the step of further administering to said individual anti-cancer radiation therapy.

7. The method of claim 1 wherein said cancer is a glioma.

8. The method of claim 1 further comprising the step of administering to said individual a therapeutically effective amount of a tricarboxylate transporter inhibitor.

9. The method of claim 5 wherein different anti-cancer compound is an anti-cancer antibody.

10. A method of treating an individual who has been identified as having cancer that comprises cancer cells that have a high rate of aerobic glycolysis by PET imaging using $^{18}$fluoro-deoxyglucose comprising the step of administering to said individual a therapeutically effective amount of an ATP citrate lyase inhibitor, wherein said therapeutically effective amount of ATP citrate lyase inhibitor is sufficient to inhibit ATP citrate lyase activity in said cancer cells to result in inhibition of conversion of citrate into oxaloacetic and acetyl-CoA in said cancer cells, leading to hyperpolarization of mitochondria and increased reactive oxygen species production sufficient to cause said cell to undergo apoptosis
wherein said cancer is selected from the group consisting of glioma, prostate cancer, bladder cancer, renal cancer and lung cancer.

11. The method of claim 10 comprising the step of administering to said individual a therapeutically effective amount of (-) hydroxycitrate.

12. The method of claim 10 wherein said cancer is a glioma.

13. The method of claim 10 wherein said ATP citrate lyase inhibitor is administered in conjunction with administration of a different anti-cancer compound.

14. The method of claim 13 wherein different anti-cancer compound is an anti-cancer antibody.

15. The method of claim 10 wherein said ATP citrate lyase inhibitor is administered in conjunction with administration of anti-cancer radiation therapy.

16. The method of claim 10 wherein the individual was identified as having cancer that comprises cancer cells that are not dependent on endogenously synthesized fatty acid and that have a high rate of aerobic glycolysis.

17. The method of claim 10 wherein the individual was diagnosed as having cancer prior to PET imaging using $^{18}$fluoro-deoxyglucose.

18. The method of claim 1 comprising the steps of:
diagnosing the individual as having cancer; subsequently
identifying said cancer as a cancer that comprises cancer cells that have a high rate of aerobic glycolysis using PET imaging with $^{18}$fluoro-deoxyglucose, and subsequently
administering to said individual the therapeutically effective amount of an ATP citrate lyase inhibitor.

19. The method of claim 18 wherein ATP citrate lyase inhibitor is (-) hydroxycitrate.

20. The method of claim 18 wherein said cancer is a glioma.

21. A method of treating an individual who has glioma that comprises cancer cells that have a high rate of aerobic glycolysis, the method comprising the steps of:
identifying an individual as an individual who has glioma;
confirming that the individual has glioma by PET imaging using $^{18}$fluoro-deoxyglucose, wherein said PET imaging using $^{18}$fluoro-deoxyglucose indicates that the glioma comprises cancer cells that have a high rate of aerobic glycolysis , and subsequently
administering to said individual a therapeutically effective amount of an ATP citrate lyase inhibitor, wherein said therapeutically effective amount of said ATP citrate lyase inhibitor is sufficient to inhibit ATP citrate lyase activity in said cancer cells to result in inhibition of conversion of citrate into oxaloacetic and acetyl-CoA in said cancer cells, leading to hyperpolarization of mitochondria and increased reactive oxygen species production sufficient to cause said cell to undergo apoptosis.

22. The method of claim 21 wherein said ATP citrate lyase inhibitor is (-) hydroxycitrate.

23. A method of treating an individual who has cancer that comprises cancer cells that have a high rate of aerobic glycolysis, the method comprising the steps of:
identifying an individual who has been determined to have cancer that comprises cancer cells that have a high rate of aerobic glycolysis that was detected by PET imaging using $^{18}$fluoro-deoxyglucose; and
administering to said individual a therapeutically effective amount of an ATP citrate lyase inhibitor, wherein said ATP citrate lyase inhibitor induces cancer cells to die
wherein said cancer is selected from the group consisting of glioma, prostate cancer, bladder cancer, renal cancer and lung cancer.

24. The method of claim 23 comprising the step of administering to said individual a therapeutically effective amount of (-) hydroxycitrate.

25. The method of claim 23 wherein said ATP citrate lyase inhibitor is administered in conjunction with administration of a different anti-cancer compound.

26. The method of claim 25 wherein different anti-cancer compound is an anti-cancer antibody.

27. The method of claim 23 wherein said ATP citrate lyase inhibitor is administered in conjunction with administration of anti-cancer radiation therapy.

28. The method of claim 23 wherein said cancer is a glioma.

29. The method of claim 23 comprising the step of administering to said individual a therapeutically effective amount of (-) hydroxycitrate.

* * * * *